(12) United States Patent
Richey, II et al.

(10) Patent No.: US 6,805,122 B2
(45) Date of Patent: *Oct. 19, 2004

(54) OXYGEN CONSERVING DEVICE UTILIZING A RADIAL MULTI-STAGE COMPRESSOR FOR HIGH-PRESSURE MOBILE STORAGE

(75) Inventors: Joseph B. Richey, II, Chagrin Falls, OH (US); Gerald G. Goertzen, Brunswick, OH (US)

(73) Assignee: Invacare Corporation, Elyria, OH (US)

( * ) Notice: Subject to any disclaimer, the term of this patent is extended or adjusted under 35 U.S.C. 154(b) by 251 days.

This patent is subject to a terminal disclaimer.

(21) Appl. No.: 09/952,763

(22) Filed: Sep. 14, 2001

(65) Prior Publication Data

US 2002/0014237 A1 Feb. 7, 2002

Related U.S. Application Data

(63) Continuation-in-part of application No. 09/695,612, filed on Oct. 24, 2000, which is a continuation-in-part of application No. 09/154,442, filed on Sep. 16, 1998, now Pat. No. 6,302,107, which is a continuation-in-part of application No. 08/942,063, filed on Oct. 1, 1997, now Pat. No. 5,988,165.

(51) Int. Cl.$^7$ .............................. A62B 7/00; A62B 9/00
(52) U.S. Cl. ............................ 128/205.18; 128/205.11; 128/205.12
(58) Field of Search .................... 128/200.24, 204.18, 128/205.11, 205.12, 205.18, 205.27, 204.22, 204.24, 204.25, 204.26; 141/2–4, 18, 21; 95/100; 96/130; 417/27, 243, 244

(56) References Cited

U.S. PATENT DOCUMENTS

| 2,944,627 A | 7/1960 | Skarstrom |
| 3,313,091 A | 4/1967 | Berlin |
| 3,898,047 A | 8/1975 | Cramer |

(List continued on next page.)

FOREIGN PATENT DOCUMENTS

| EP | 239 713 | 10/1987 | |
| EP | 860 647 A | 8/1998 | |
| GB | 374 540 A | 6/1932 | |
| JP | 63-307101 | 12/1988 | |
| JP | 64-28208 | 1/1989 | |
| WO | 83/03983 | 11/1983 | |
| WO | WO87/01599 | * 3/1987 | ............ 128/204.18 |
| WO | WO 99/16529 | 4/1999 | |

Primary Examiner—Weilun Lo
Assistant Examiner—Joseph F. Weiss, Jr.
(74) Attorney, Agent, or Firm—Nenad Pejic; Calfee, Halter & Griswold

(57) ABSTRACT

An apparatus and process for supplying low pressure oxygen-enriched gas to a patient and at a moderate pressure to a radial compressor, whereupon it is compressed and fed to a high pressure storage tank. The oxygen-enriched gas is prioritized so that it is continuously supplied via a patient flow line to the patient.

24 Claims, 13 Drawing Sheets

U.S. PATENT DOCUMENTS

| | | | |
|---|---|---|---|
| 3,924,968 A | * 12/1975 | Gaines et al. | 417/53 |
| 3,964,866 A | 6/1976 | Shelby | |
| 4,013,429 A | 3/1977 | Sircar et al. | |
| 4,194,890 A | 3/1980 | McCombs et al. | |
| 4,222,750 A | 9/1980 | Gauthier et al. | |
| 4,263,018 A | 4/1981 | McCombs et al. | |
| 4,331,455 A | 5/1982 | Sato | |
| 4,349,357 A | 9/1982 | Russell | |
| 4,353,682 A | * 10/1982 | Linnert et al. | 417/295 |
| 4,428,372 A | 1/1984 | Reysel et al. | |
| 4,449,990 A | 5/1984 | Tedford, Jr. | |
| 4,465,436 A | * 8/1984 | Schonwald | 417/271 |
| 4,516,424 A | 5/1985 | Rowland | |
| 4,552,571 A | 11/1985 | Dechene | |
| 4,576,616 A | * 3/1986 | Mottram et al. | 55/68 |
| 4,610,700 A | 9/1986 | Miller et al. | |
| 4,627,860 A | 12/1986 | Rowland | |
| 4,636,226 A | 1/1987 | Canfora | |
| 4,670,223 A | 6/1987 | Delachapelle | |
| 4,673,415 A | 6/1987 | Stanford | |
| 4,698,075 A | 10/1987 | Dechene | |
| 4,706,664 A | 11/1987 | Snook et al. | |
| 4,765,804 A | 8/1988 | Lloyd-Williams et al. | |
| 4,844,059 A | 7/1989 | Koch | |
| 4,867,766 A | 9/1989 | Campbell et al. | |
| 4,869,733 A | 9/1989 | Stanford | |
| 4,880,443 A | 11/1989 | Miller et al. | |
| 4,905,685 A | 3/1990 | Olsson et al. | |
| 4,922,900 A | 5/1990 | Kiske et al. | |
| 4,948,391 A | 8/1990 | Noguchi | |
| 4,957,107 A | * 9/1990 | Sipin | 128/204.21 |
| 4,979,882 A | * 12/1990 | Wipf | 417/410 |
| 4,983,190 A | 1/1991 | Verrando et al. | |
| 4,991,616 A | 2/1991 | Fabregat | |
| 5,071,453 A | 12/1991 | Hradek et al. | |
| 5,078,757 A | 1/1992 | Rottner et al. | |
| 5,144,945 A | 9/1992 | Nishino et al. | |
| 5,154,737 A | 10/1992 | Jenkins et al. | |
| 5,163,978 A | 11/1992 | Leavitt et al. | |
| 5,195,874 A | 3/1993 | Odagiri | |
| 5,199,423 A | 4/1993 | Harral et al. | |
| 5,207,806 A | 5/1993 | Lagree et al. | |
| 5,237,987 A | 8/1993 | Anderson et al. | |
| 5,248,320 A | 9/1993 | Garrett et al. | |
| 5,354,361 A | 10/1994 | Coffield | |
| 5,474,595 A | 12/1995 | McCombs | |
| 5,490,871 A | 2/1996 | Coates et al. | |
| 5,531,807 A | 7/1996 | McCombs | |
| 5,584,669 A | 12/1996 | Becker | |
| 5,593,478 A | 1/1997 | Hill et al. | |
| 5,704,964 A | 1/1998 | Kaneko et al. | |
| 5,730,778 A | 3/1998 | Hill et al. | |
| 5,823,186 A | * 10/1998 | Rossen et al. | 128/204.21 |
| 5,858,062 A | 1/1999 | McCulloh et al. | |
| 5,893,944 A | 4/1999 | Dong | |
| 5,988,165 A | * 11/1999 | Richey, II et al. | 128/205.12 |
| 6,132,177 A | * 10/2000 | Loprete et al. | 417/221 |
| 6,302,107 B1 | * 10/2001 | Richey, II et al. | 128/205.18 |
| 6,422,237 B1 | * 7/2002 | Engel et al. | 128/204.21 |

* cited by examiner

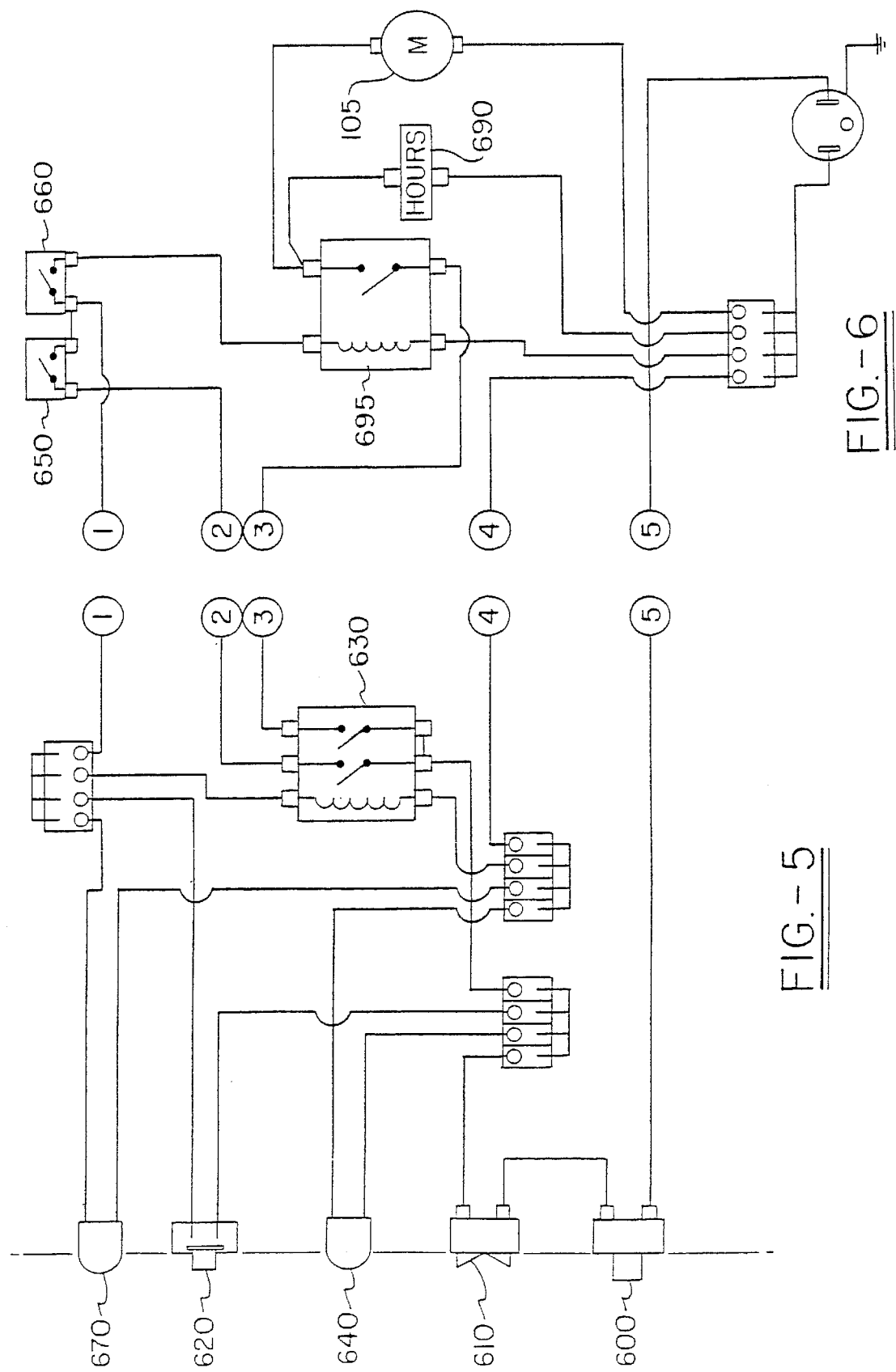

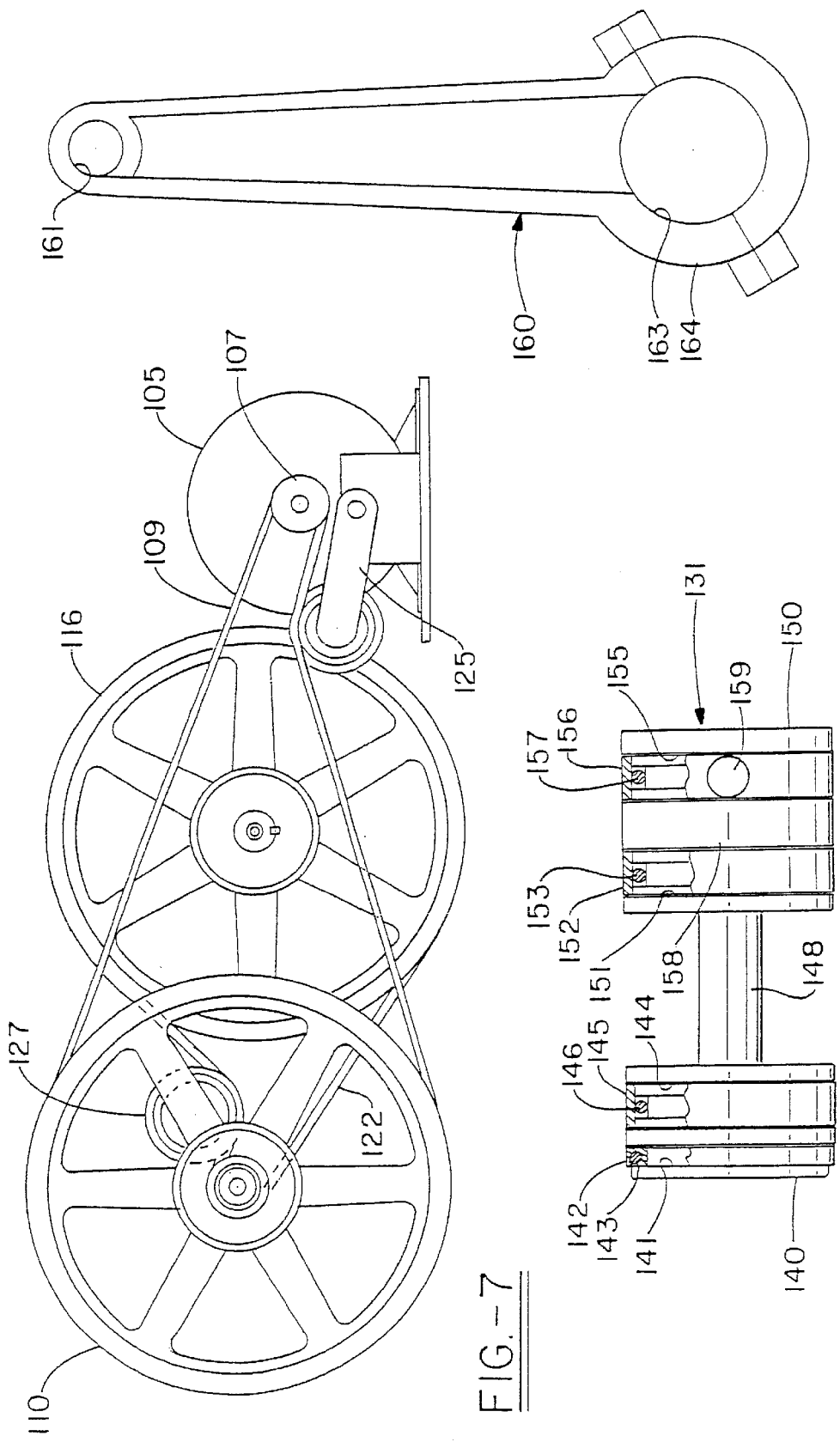

OXYGEN CONSERVING DEVICE UTILIZING A RADIAL MULTI-STAGE COMPRESSOR FOR HIGH-PRESSURE MOBILE STORAGE

CROSS REFERENCE

This application is a continuation-in-part of pending U.S. Ser. No. 09/695,612, filed Oct. 24, 2000 for Oxygen Conserving Device Utilizing a Radial Multi-Stage Compressor for High-Pressure Mobile Storage, which in turn is a continuation-in-part U.S. Ser. No. 09/154,442, filed Sep. 16, 1998, now U.S. Pat. No. 6,302,107 for "Apparatus and Method for Forming Oxygen-Enriched Gas and Compression Thereof for High Pressure Mobile Storage Utilization", which in turn is a continuation-in-part of U.S. Ser. No. 08/942,063, filed Oct. 1, 1997, now U.S. Pat. No. 5,988,165 for "Apparatus and Method for Forming Oxygen-Enriched Gas and Compression Thereof for High Pressure Mobile Storage Utilization".

FIELD OF INVENTION

The present invention relates to an apparatus and process for conserving enriched oxygen which is subsequently collected under high pressure in a portable container for ambulatory patient use and to permit facile patient mobility. A multi-stage radial compressor is utilized to pressurize the desired gas. The enriched oxygen is fed at a reduced pressure from a product storage tank to a patient, and at the storage tank pressure to generally a buffer tank and subsequently to a radial compressor.

BACKGROUND OF THE INVENTION

Heretofore, oxygen concentrators have been utilized to supply patients with a gas having a high oxygen concentration for extended periods of time. Oxygen concentrators typically produce a breathable gas containing from about 80 percent to about 96 percent oxygen from atmospheric air and thus have been widely utilized in the home health care field.

U.S. Pat. No. 4,627,860, to Rowland, relates to a microprocessor and cooperating means for monitoring or sensing functions and performance of various components of the concentrator. A test apparatus having means for selecting any of the functions monitored by the microprocessor is connected to the concentrator and displays the selected monitored functions for diagnosing performance levels and component problems or failures.

U.S. Pat. No. 5,071,453, to Hradek et al. relates to an oxygen concentrator which is intended for aircraft use. A booster compressor is used to increase the pressure of the product gas from the concentrator in order to increase the amount of the gas which can be stored in a plenum. The booster includes two moving pistons which are rigidly linked together and a series of check valves which control the flow of gases through the compressor. One of the pistons is driven by air from the rotary valve in the concentrator, and the other piston compresses the product gas for delivery to the plenum. A small sample of concentrator product gas is monitored by an oxygen sensor for oxygen concentration. Once the oxygen concentration has reached an acceptable level, the booster compressor fills the plenum with product gas. Thereafter, if the oxygen concentration of product gas delivered to the crew from the concentrator falls below the concentration which is required at a particular altitude, the product gas stored in the plenum is delivered to the crew. The oxygen sensor monitors the concentrator output product gas to the breathing regulator when the stored plenum gas is not being used.

U.S. Pat. No. 5,354,361, to Coffield, relates to a pressure-swing adsorber system including a pneumatically driven booster compressor to increase the pressure of the output product gas. A pair of inlet valves controls feed air flow to the sieve beds and the drive cylinder of the booster compressor and are cycled so that one valve opens to pressurize one sieve bed before the other valve closes to allow the other sieve bed to vent to atmosphere. During the time that both valves are open, the pressure in the two sieve beds and on opposite sides of the drive cylinder equalize and a portion of the gas in the pressurized sieve bed and drive cylinder side is captured rather than being vented to ambient. System efficiency is increased by selecting whether captured gas from the last pressurized sieve bed or drive cylinder side reaches the next to be pressurized sieve bed first.

U.S. Pat. No. 5,858,062, assigned to Litton Systems, Inc., relates to an apparatus for providing oxygen-enriched air at a first pressure and at a second pressure, the second pressure being greater than the first pressure. The apparatus comprises, in combination, a pressure swing adsorption system and a pressure intensifier. The pressure swing adsorption system for enriching the oxygen content of air has a pressure of at least the first pressure. The pressure swing adsorption system is adapted to provide oxygen-enriched air to a first outlet at the first pressure and to provide oxygen-enriched air to a pressure intensifier at the first pressure. The pressure intensifier pressurizes the oxygen-enriched air and provides the oxygen-enriched air to a second outlet at the second pressure.

SUMMARY OF THE INVENTION

It is an aspect of the present invention to provide a method and apparatus for storing high-pressure, high-purity oxygen in a pressure vessel for use in the home health care or related fields as for ambulatory patients, persons confined to wheelchairs, and those who are bedridden.

In accordance with the invention there is provided a method and apparatus for producing from air an oxygen-enriched gas and initially storing the same in a concentrator product tank. At least a portion of the oxygen-enriched gas is fed by different methods as to an optional but desired compressor buffer tank where it is stored. After reaching a predetermined pressure, the gas is fed to a compressor where it is compressed to a high pressure and stored in a mobile or portable high-pressure container. A patient can thus have increased mobility through use of the portable, one or more high-pressure oxygen containers, which can be filled in one's own home.

It is a further aspect of the invention to provide circuitry to assure prioritization of the flow rate and concentration of the enriched gas to a patient. The excess gas, when available, is simultaneously delivered to an independent, multi-stage compressor.

In accordance with another aspect of the invention there is provided a home health care oxygen concentrator for physically separating molecules of oxygen from air with oxygen in a subsequent operation being fed to a high-pressure vessel. The concentrator comprises one or more molecular sieve beds containing a physical separation material, a first (i.e., feed stock) compressor to provide a feed source of compressed air, control means which regulate the product gas flow through the beds to a concentrator product tank, a second enriched-gas storage tank (e.g., a buffer tank), and a second compressor, e.g., multi-stage, which is not operated by the first compressor but operates independently thereof and enables the oxygen-enriched gas to be compressed and fed to a high-pressure vessel or container.

In a further embodiment, a radial compressor can be utilized to compress oxygen from an optional but desired buffer tank connected to an oxygen source. The radial compressor has pistons radially arranged around a central drive shaft and compresses the oxygen to a high pressure and stores the same in a compact storage cylinder. This design is more compact and less bulky than typical linear designed compressors, and allows the compressor to be housed in a relatively small unit which is thus more easily transportable. An oxygen sensor determines whether a required minimum oxygen concentration is being supplied to a patient and if not, terminates the flow of compressed oxygen to the cylinder, while maintaining the flow to the patient.

Still another embodiment relates to an oxygen storage tank which operatively feeds oxygen-enriched gas to a patient and which also independently and operatively feeds enriched oxygen at a different and generally greater pressure to a buffer tank where subsequently it is compressed by a compressor, independent of an initial compressor for feeding air to the molecular sieves.

BRIEF DESCRIPTION OF THE DRAWINGS

FIG. 5 is a schematic showing one portion of a control circuit for operating a multiple-stage compressor of the present invention;

FIG. 6 is a schematic of the remaining portion of the control circuit of FIG. 5 for operating a multiple-stage compressor of the present invention;

FIG. 7 is a side elevational view of the compression apparatus of the present invention;

FIG. 9 is a side elevational view of the upper portion of the two-part piston assembly of the present invention;

FIG. 10 is a side elevational view of the bottom portion of the two-part piston assembly of the present invention.

DETAILED DESCRIPTION OF THE PREFERRED EMBODIMENT

While a preferred embodiment of the invention is described hereinbelow, it is to be understood that the various aspects and parameters of the present invention can vary and be different such as the pressure and purity of the oxygen-enriched gas exiting from a concentration product tank, the pressure at which the enriched gas is fed to the patient and its flow rate, the pressure maintained in a buffer tank, the pressure at which the compressor initially draws enriched gas from the buffer tank, the buffer tank pressure at which the compressor shuts off, and the like. Moreover, while reference is made to a particular oxygen concentrator as set forth immediately below, generally any type of oxygen concentrator can be utilized which yields a source of enriched air containing anywhere from about 50 percent oxygen up to about 99 percent by volume.

Figure 1:
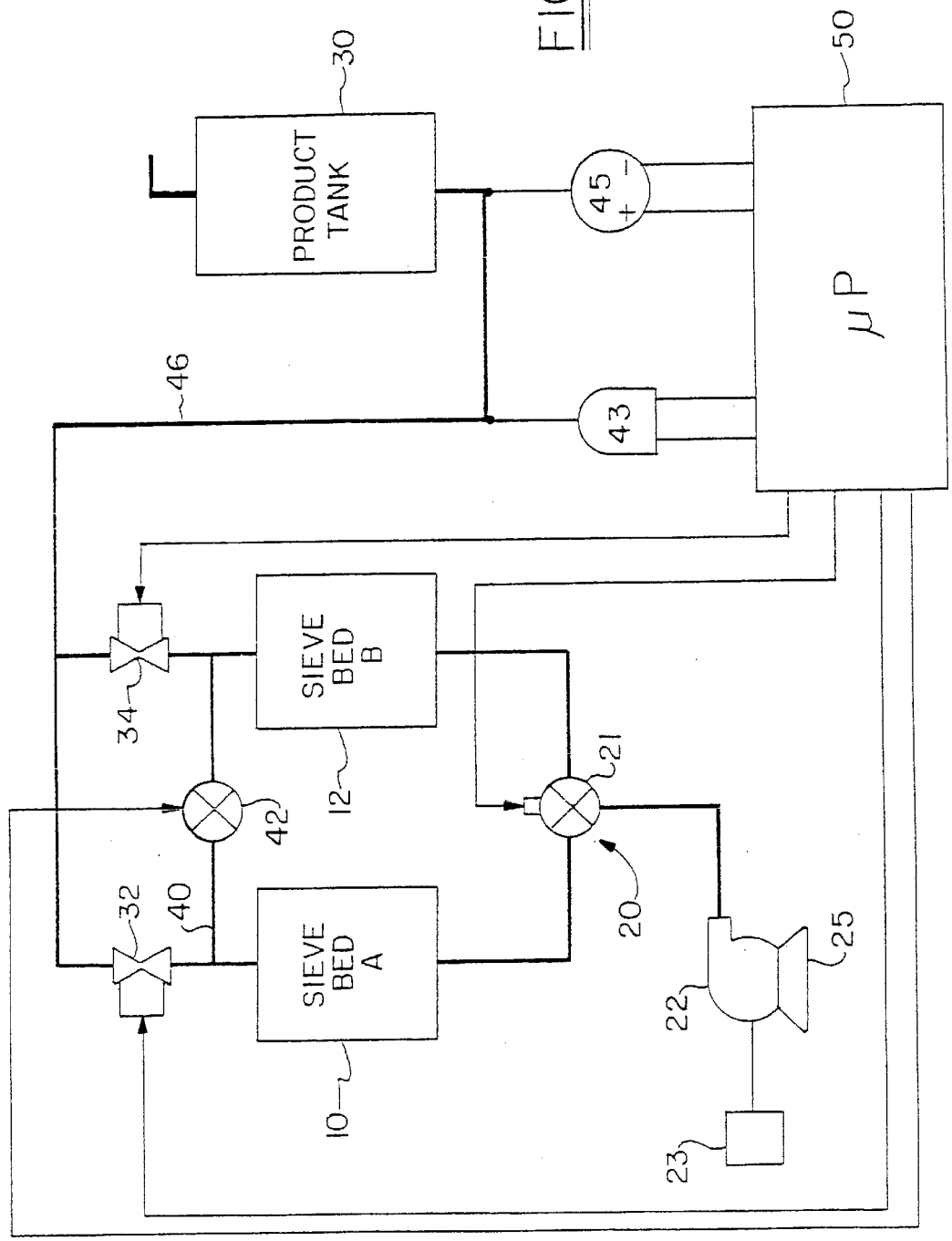
FIG. 1 is a block diagram of an oxygen concentrator for separating oxygen from a gaseous mixture such as air.

With reference to FIG. 1, the apparatus includes one or more, and preferably two beds 10 and 12 which contain a physical separation medium or material. The separation material selectively adsorbs one or more adsorbable components as from air and passes one or more nonadsorbable components of such a gaseous mixture. The physical separation material can be a molecular sieve with pores of uniform size and essentially the same molecular dimensions. These pores selectively adsorb molecules in accordance with molecular shape, polarity, degree of saturation, and the like. In the preferred embodiment, the physical separation medium is an aluminasilicate composition with 4 to 5 A (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13x zeolite. The zeolite adsorbs nitrogen, carbon monoxide, carbon dioxide, water vapor, and other significant components of air.

A cross-over valving means 20, which preferably includes a four-way valve 21, selectively and cyclically connects the inlet end of two beds, one at a time, during a production phase with a source of the gas mixture, e.g., air under pressure supplied from a first compressor 22 (i.e., the feed compressor), while the other bed is vented to atmosphere during a purge phase. Specific to the preferred embodiment, the cross-over valving means selectively connects one of the beds in fluid communication with an air pump or compressor 22 which supplies air from about 15 to about 21 psi. As used herein, "fluid communication" refers to means allowing flow of the appropriate gases. Of course, vacuum can also be used during the purge phase with the present invention to enhance evacuation. Compressor 22, which receives air from inlet 23, is connected to a first drive motor 25, in the preferred embodiment about a ¼-horsepower electric motor. A solenoid (not shown) or other cross-over valve actuating means selectively causes the cross-over valving means to move alternately between first and second positions. In the first position, the first bed 10 is connected with compressor 22 to cause nitrogen adsorption and oxygen enrichment in the product gas, and the second bed 12 is vented to atmosphere to allow evacuation. In the second position, the first bed is vented to atmosphere to allow evacuation and the second bed is connected with the air compressor to cause nitrogen adsorption. The invention is described with specific reference to a pressure-swing control. However, it is equally applicable to other methods of sequencing the gas flow through the sieve beds such as a timing-based system.

The composition of the gas in the voids of the zeolite varies from substantially pure primary-product gas at the outlet end, to the ambient gaseous mixture composition at the inlet end. As the gas mixture is introduced through a bed inlet to an adsorbed, gas-free or regenerated bed, an adsorption zone of finite, relatively large size is formed. This adsorption zone is a region of the bed in which the full capacity of the adsorbent to hold the adsorbable components has not been reached. This adsorption zone moves from the bed inlet toward a bed outlet with a velocity significantly less than the superficial gas velocity in the bed. When the adsorption zone reaches the outlet end of the bed, adsorbable components begin to flow through the bed outlet into the nonadsorbable primary product stream. This time is hereinafter referred to as the "breakthrough." For a given gaseous composition, the breakthrough is defined by the size and configuration of the bed container as well as the packing configuration of the molecular sieve and the flow rate and bed gas pressure. The configuration of the bed is generally cylindrical and the output volume rate can vary from about 0.1 to 6 liters per minute. The breakthrough is the time required for the diffusion reaction as the nitrogen saturates and is weakly bonded to the sieve bed. When breakthrough occurs, primary product-enriched bed gas in the zeolite voids varies from a higher primary product gas concentration at the bed outlet to a lower concentration at the bed inlet. In the preferred embodiment, the primary product-enriched bed gas is about 80 percent primary product at breakthrough. While adsorption is occurring in one bed, the adsorbable components adsorbed by the separation medium of the other bed are purged from the other bed because of the drop in pressure due to atmospheric venting and because of exposure to relatively pure product gas from the first tank.

The first bed 10 is connected with a reservoir or product tank 30 by way of a first check valve 32 or other unidirectional valving means. The first check valve 32 permits the primary product gas from the first bed 10 to flow into the reservoir or product tank 30 via line 46 when the product gas pressure in the first bed 10 exceeds the pressure of product gas in the reservoir or product tank 30. The first check valve prohibits the product gas from flowing from the reservoir or product tank 30 when the pressure in the first bed 10 is lower than the reservoir or product tank. More specific to the preferred embodiment, the check valve imposes a 1.5 psi bias such that flow is only permitted when the pressure in the first bed exceeds the pressure in the reservoir or product tank by 1.5 psi. The second bed 12 is connected with the reservoir or product tank 30 by way of a second check valve 34 or other unidirectional valving means. The second check valve 34 again provides for unidirectional flow of the primary product gas from the second bed 12 to the reservoir or product tank 30.

A pressure equalization flow path 40 extends between outlets of the first and second beds. A concentration equalization valve 42 is either open or closed to selectively permit or prevent gas flow through the flow path between the first and second beds. A control means 50 cyclically causes the cross-over valve actuating means (i.e., two solenoids) and the concentration equalization valve 42 to be operated. The control means periodically and cyclically enables a concentration equalization valve actuator which is also a solenoid.

Oxygen sensor 43 registers the oxygen concentration of the product gas and can be located in the product tank 30. The sensor 43 communicates a sensed value to the microprocessor (i.e., control means). Similarly, a pressure sensor 45 registers the pressure in the product tank and communicates the same to the microprocessor.

The control means causes the cross-over valving means 20 to alternate between its first and second positions for the appropriate period during each cycle segment. A cycle segment can be either the product gas generation cycle or the purge cycle. The cycle duration is selected such that each bed is connected with the source of air for a period of time which is equal to or less than the breakthrough time. The mechanism which triggers the cross-over valving can be based on the pressure, such as a pressure set point or set point range, in the bleed line from the product tank as is used in a pressure-based control cycle, or it can be based strictly on a residence time from the product-producing bed, such as in a timing cycle-based control cycle. In accordance with another embodiment of the invention, the control cycle can utilize variable pressure in order to achieve a residence time within a defined range based upon a projected breakthrough time. In the preferred embodiment, the beds are 3.5 inches in diameter, 15 inches in length, and each contains 6.5 pounds of 5A zeolite.

The gas mixture is supplied at up to 21 psi of pressure to the first bed. Concurrently, the second bed (i.e., a "used" bed) is vented to atmosphere to cause purging of the nitrogen-enriched molecular sieves. Before the breakthrough time, the concentration equalization valve is opened allowing primary product-enriched gas from the first bed to flow into the evacuated second bed. During the concentration equalization period, one bed is evacuated and the other has just reached the pressure set point which drives flow between the beds. The flow is of high oxygen content so that the first product to pass into the product tank via line 46 is essentially product gas produced by the oxygen beds. The second bed pressure is product-enriched gas to purge the sieve bed. Before the primary product-enriched gas from the first bed is evacuated through the second bed, the cross-over valving means 20 is actuated to reverse its position. Actuating the cross-over valving means discontinues supplying of the gaseous mixture to the first bed and commences evacuating it and concurrently discontinues evacuating the second bed and commences supplying it with the gaseous mixture.

Subsequent to the actuation of the cross-over valving means, the concentration equalization valve 42 remains open to continue allowing a purge supply of product-enriched gas to flow into the second bed. This equalizes the concentration of gas which is supplied to the product tank since the cycling is sequenced so that the product gas proceeds from the breakthrough zone to flow into the product tank. Subsequently, the concentration equalization valve closes and terminates the flow of primary-product gas between the beds. In the second segment of the cycle, the pressure in the second bed increases approaching the gas mixture source pressure. Concurrently, the pressure in the first bed decreases approaching atmospheric pressure.

Before the secondary product molecules have traversed the second bed, the concentration equalization valve 42 is opened allowing the primary product-enriched gas in the zeolite voids of the second bed to flow to the first bed. While the primary product-enriched gas is flowing to the first bed, the cross-over valving means is actuated. Actuating the cross-over valving means discontinues the evacuation of the first bed and commences supplying the gaseous mixture and concurrently discontinues supplying the gaseous mixture to the second bed and commences evacuating it. Subsequent to actuating the cross-over valving means, the concentration equalization valve is closed terminating the pressure equalizing flow of the primary product-enriched gas between the beds. The steps are cyclically repeated to provide continuing fractionating of the primary product gas from the mixture.

Referring again to FIG. 1, in a preferred embodiment the reservoir or product tank 30 maintains a reservoir of oxygen at a minimum pressure of about 14 psi. The oxygen-enriched gas contains from about 50 to about 99 percent, desirably from about 70 to about 98 percent, and preferably from about 84 to about 96 percent by volume of oxygen. In accordance with conventional procedures, product tank 30 can be connected to a pressure regulator (not shown) for controlling the pressure of the oxygen to a patient. Typically a pressure of 5 psi is utilized. A flow meter (also not shown in FIG. 1) can be utilized to limit the flow rate to the patient such as from 0.1 to about 6 liters per minute with a flow rate of about 3 liters per minute often being utilized. If desired, a humidifier (not shown) can add moisture to the oxygen-enriched gas. The gas is delivered to the patient via tubing and breathing apparatus which can be inserted into the patient's nostrils.

In accordance with other concepts of the present invention, oxygen-enriched gas from an oxygen concentrator such as that described hereinabove can be fed in any variety of methods to a compressor where it is compressed to very high pressure and stored in a portable or mobile container such as a gas cylinder.

Figure 2:
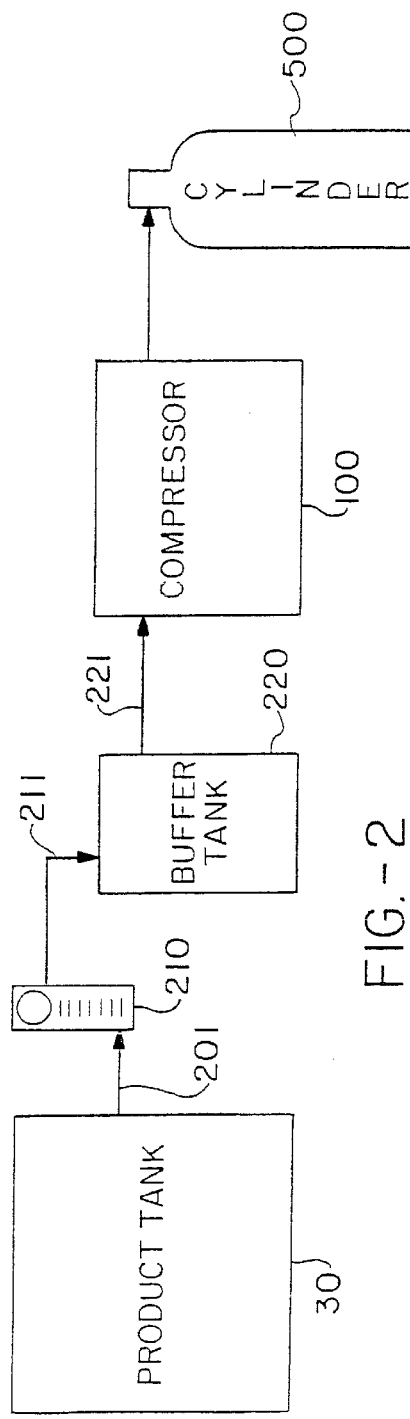
FIG. 2 is a block diagram of an apparatus and process in accordance with the present invention for compressing oxygen-enriched air and feeding it to a portable container.

In the embodiment of FIG. 2, all of the oxygen-enriched gas is fed to a compressor. A concentrator (not shown but such as described hereinabove) has an oxygen-enriched product tank 30 wherein the pressure can vary as from about 14 to about 21 psi. The oxygen-enriched gas therein is fed via line 201 to a flow meter 210 at the pressure of the concentrator tank, that is from about 14 to about 21 psi. Flow meter 210 controls the flow rate of the oxygen-enriched gas which is fed via line 211 to buffer tank 220 wherein the gas pressure therein can also range from about 14 to about 21 psi. Via line 221, the predominantly oxygen gas is fed to compressor 100. Compressor 100, in a manner described below, compresses the oxygen-enriched gas to a pressure of about 2,250 psi and stores it within a mobile or portable cylinder 500. Depending upon the withdrawal rate of the oxygen-enriched gas by the compressor, the feed pressure thereto can range from 21 psi down to a predetermined cut-off pressure such as about 5 or 7 psi whereupon the compressor is automatically shut off by a pressure sensor switch.

Figure 3:
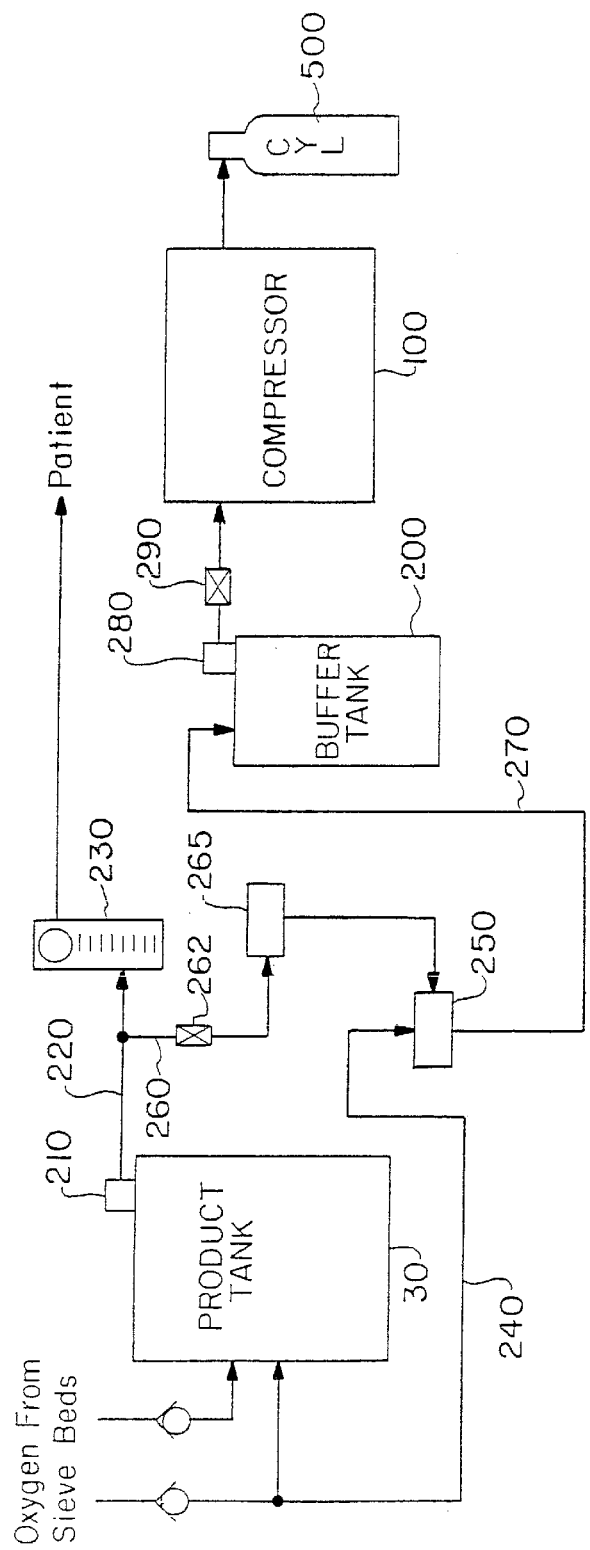
FIG. 3 is a block diagram of the apparatus and process of the present invention for feeding a portion of enriched gas at a controlled rate to a patient and another portion of the enriched gas to a compressor for high-pressure storage in a portable container.
Figure 4:
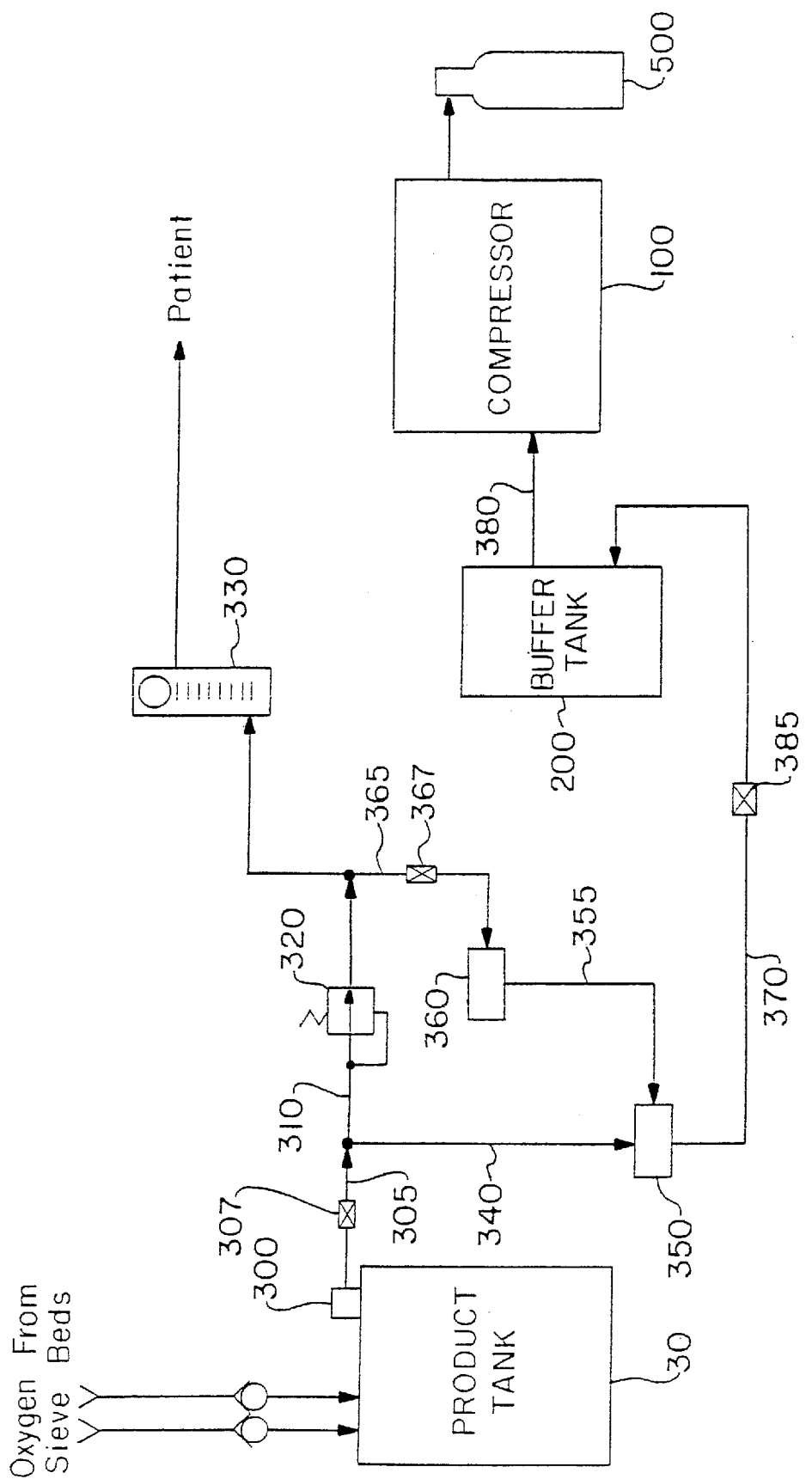
FIG. 4 is a block diagram of the apparatus and process of another embodiment of the present invention for feeding a portion of enriched gas at a controlled rate to a patient and another portion of the enriched gas to a compressor for high-pressure storage in a portable container.

FIGS. 3 and 4 relate to embodiments wherein oxygen-enriched air from product tank 30 of the oxygenator is fed by various methods desirably to a buffer tank of the compressor but prioritized as with regard to oxygen concentration and/or a sufficient pressure. For example, the feed rate to a patient can vary from between 0.1 and 6 liters per minute at a pressure of a predetermined value such as 5 psi with the remaining oxygen-enriched gas generally being fed at a different pressure to the buffer tank. The buffer tank can generally contain a broad range of pressure therein such as, for example, between 14 and 21 psi. However, as noted with regard to FIG. 2, depending upon the withdrawal rate of the gas in the buffer tank by the compressor, the pressure thereof can drop down to a predetermined cut-off pressure, such as 7 psi, which is higher than the pressure of the gas being fed to the patient to ensure an adequate flow of the oxygen-enriched gas to the patient.

Referring to the embodiment of FIG. 3, a 5-psi regulator 210 emits oxygen-enriched gas from product tank 30 into flow line 220 and feeds the same to flow meter 230 which subsequently emits the oxygen-enriched gas to the patient at a predetermined flow rate of from 0.1 to 6 liters per minute. Optionally, the flow meter can be closed so that all the enriched oxygen is directed to the compressor. Gas not directed to the patient is carried via line 240 to two-way valve 250. A very small portion of the gas in line 220 is directed through line 260 through restrictor 262 into oxygen sensor 265 which detects whether or not the concentration of the oxygen is of a predetermined value such as is at least 84 percent. When the oxygen sensor detects a concentration at or above the predetermined level, two-way valve 250 is open and permits the oxygen-enriched gas to flow through line 270 into buffer tank 200 wherein the pressure is essentially the same as the oxygen product tank pressure. However, should the oxygen sensor not detect a suitable oxygen concentration, two-way valve 250 is closed so that the oxygen concentrator can build up a sufficient oxygen concentration. This arrangement prioritizes the flow of oxygen-enriched gas so that the patient is assured of receiving a gas having a minimum oxygen concentration therein. Buffer tank 200 can have a regulator 280 thereon generally set at 12 psi to admit the oxygen-enriched gas to the compressor when needed. Alternatively, the pressure regulator can be set at anywhere from about 13 to about 21 psi. Restrictor 290 controls the flow rate of gas from the buffer tank to the compressor. Should the compressor drop the pressure in the buffer tank to below a predetermined value, a pressure sensor (not shown) will automatically cut off the flow of gas at a pressure above the pressure of the gas being fed to the patient. This prioritization assures that the patient receives priority with regard to oxygen-enriched gas.

The embodiment of FIG. 4 emits the oxygen-enriched gas through a 14 to about an 18-psi regulator 300 into flow line 305 having flow rate restrictor 307. The flow is then split with a portion via line 310 going through 5-psi regulator 320 and into flow meter 330 which then directs the gas to the patient at a desired flow rate of generally from 0.1 to 6 liters per minute, although optionally the flow meter can be closed. The remaining portion of the gas is directed via line 340 to two-way valve 350. A small portion of the gas going to the patient is diverted through line 365 through flow restrictor 367 to oxygen sensor 360. As in FIG. 3, the oxygen sensor is set at a predetermined value such as a concentration of 84 percent so that when the level is not achieved, two-way valve 350 is closed through electrical line 355. This aspect allows the amount of oxygen in the concentrator tank to be increased by the oxygenator unit. The same prioritizes the concentration of oxygen to ensure that the patient receives an amount of oxygen of at least the minimum predetermined value. When the oxygen concentration is sufficient, the gas flows through two-way valve 350 into line 370 and into buffer tank 200 where it is stored generally at a pressure of about 14 to 18 psi. A relief valve 385 which can be set at any desired value such as about 14 psi ensures that gas under sufficient pressure is being admitted to the buffer tank. The oxygen-enriched gas is admitted to the compressor via line 380. Should the compressor withdraw gas faster than it is being received by the buffer tank, the pressure therein will drop. A pressure sensor switch (not shown) can be set to a predetermined value (e.g., about 7 psi) to ensure or prioritize that a sufficient amount or flow of gas is being fed to the patient. The predetermined shut-off pressure of the compressor is always above the pressure of the gas being fed to the patient. The embodiment of FIG. 4 is preferred.

While the above description, as exemplified by FIGS. 2, 3, and 4, generally constitutes a preferred embodiment of the present invention, it is to be understood that the same can be modified. For example, oxygen product tank 30 need not be utilized. Instead, the oxygen-enriched air from an oxygen concentrator, such as shown in FIG. 1, can be fed to the buffer tank via the shown and described flow lines of the various embodiments such as set forth in FIGS. 2, 3, and 4. Accordingly, the oxygen-enriched air will be separated with one component directed to the patient and the other component being directed to the buffer tank. Prioritization of the oxygen-enriched gas to the patient either by a minimum oxygen concentration or a sufficient pressure in the buffer tank is still generally utilized. Alternatively, an enriched oxygen product tank 30 can be utilized and the buffer tank can optionally be eliminated. In other words, enriched oxygen from the product tank can be fed via one component to the patient and to a second component via the flow line shown to the compressor. In this situation, prioritization of the desired flow and oxygen concentration to the patient is maintained as described hereinabove with regard to either the level of oxygen concentration or an adequate pressure being admitted to the compressor.

Figure 8:
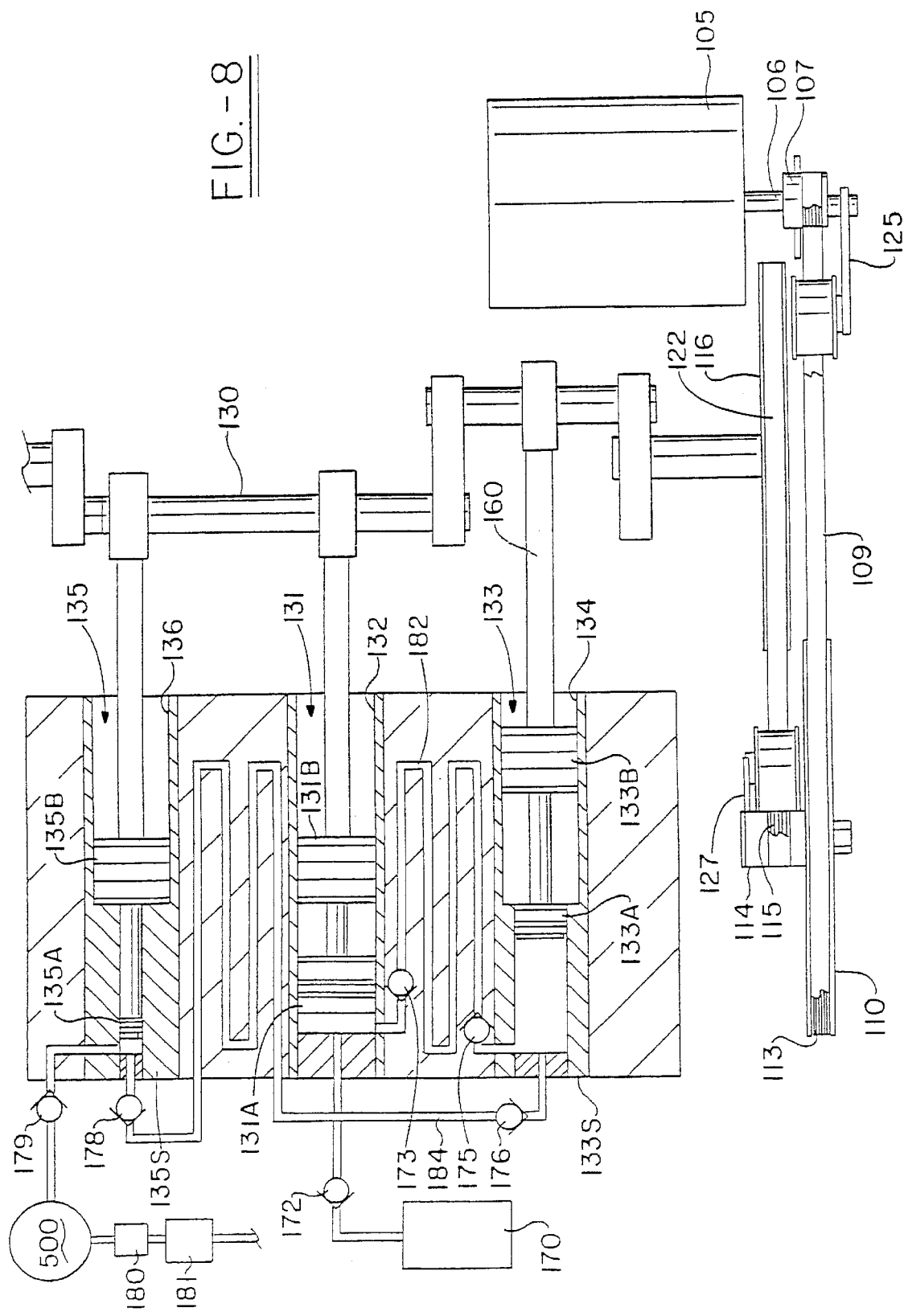
FIG. 8 is a top plan view of the compression apparatus of the present invention.

Referring now to the compressor assembly 100 as shown in FIGS. 7 and 8, it generally utilizes an AC electric-drive motor 105 which can rotate at any desired speed, e.g., 1,700 rpm. Motor 105 can contain a fan (not shown) either within the motor housing or immediately adjacent thereto to draw air through the motor to cool the same. Power is conveyed from the motor through shaft 106 to drive wheel 107. Desirably the drive wheel has a plurality of grooves therein to receive a V-belt such as main drive belt 109. Such belts are generally reinforced with fiber and have a very long life. Main drive belt 109 is connected to main gear 110 which contains a plurality of grooves 113 therein. The number of peripheral grooves 113, as well as the size and location thereof, coincides with the grooves of drive wheel 107 and matingly engage a plurality of projections located on main drive belt 109. Extending from main gear 110 is an offset hub gear 114 which has a much smaller diameter than main gear 110. Hub gear 114 also has grooves 115 thereon to receive a secondary drive V-belt 122. A second or secondary large gear 116 has grooves on the periphery thereof which matingly engage the secondary drive V-belt 122. Offset hub 114 through the secondary V-drive belt 122 contacts and serves to drive secondary gear 116 which in turn is connected to crankshaft 130.

Through the utilization of the two large gears 110 and 116, a double-reduction is obtained such that the rotational speed of crankshaft 130 is a desirably low speed such as approximately 50 rpm. Both drive belts 109 and 122 desirably have a spring-loaded idler arm 125 and 127, respectively, which applies a small amount of tension. The actual pull tension of the first belt can be about 20 pounds, whereas the tension on the second belt can be about 100 pounds.

The multi-stage compressor of the present invention can have any number of pistons, but in the present embodiment has three. As shown in FIG. 8, two of the pistons, i.e., the first and third pistons, are located on the same crankshaft lobe, whereas the second piston is located on a different lobe offset 180° from the first and third pistons. The reason for this is that pistons one and three will be drawing in air when the second piston is being compressed and vice versa. Although not shown, a crankshaft can be utilized which contains three lobes thereon, each offset from one another by approximately 110° to 130°, e.g., about 120°, so as to minimize the torque resistance applied to the motor during the compression stroke.

The compressor of the present invention has three pistons, i.e., piston #1 (131), piston #2 (133), and piston #3 (135). Each piston is contained within a separate cylinder and thus piston #1 is contained within the first cylinder (132), the second piston is contained the second cylinder (134), and the third piston is contained within the third cylinder (136). While the diameter of the head 140 of the first piston is approximately equal to the diameter of the base portion of the piston as shown in FIGS. 8 and 9, the diameter of the head of piston #2 (133) is smaller than that of piston #1, and the diameter of the head of piston #3 (135) is smaller than the diameter of piston #2 (133). However, the base of each piston 131B, 133B, and 135B is of the same size for reasons set forth hereinbelow. In order to permit pistons #2 and #3 to operate properly, each contains an annular sleeve 134S and 136S on the inside of the cylinder wall the internal diameter of which is approximately equal to the external diameter of piston heads #2 and #3 respectively.

Regardless of the size of the piston head, it has two rings as generally indicated in FIG. 9. Inasmuch as the rings of all three piston heads are generally the same, only the first piston is shown in FIG. 9. The piston head has two annular grooves or recesses therein, that is top piston annulus 141 and bottom annulus 144. The top annulus contains a U-shaped seal therein generally made out of a Teflon® alloy or other low-friction material. The seal contains a coil tension spring 143 therein which forces the seal radially outward against the cylinder wall to prevent compressed air from leaking through the piston head between the piston and the cylinder wall. To also ensure the maintenance of a good seal, seal 142 is U-shaped so that upon the build-up of pressure in the cylinder head, the compressed gas will communicate and enter into the seal and force the outer edge thereof radially outward against the cylinder wall. Piston head bottom annulus 144 contains a flat or vertical glide ring 145 which extends around the annulus and is also radially forced outwardly by a coil tension spring 146 located therein. The bottom glide ring 145 can be made out of a Teflon® alloy and serves as a piston glide ring.

Connecting rod 148 connects the piston head to piston base 150. The piston bases of all three pistons are the same diameter and accordingly engage a mating cylinder of essentially the same diameter. The piston base contains an upper base annulus 151 and a lower base annulus 155, both of which have a glide ring therein similar to if not identical to glide ring 145 of piston head annulus 144. Thus, upper base annulus 151 has a glide ring 152 therein which is forced radially outward by coil spring 153. Similarly, lower base annulus 155 has a glide ring 156 therein which is radially forced out by coil spring 157. Although three glide rings have been shown and described as being identical, they can be different and use different material, and the like. Piston base 150 contains bore 158 which extends laterally therethrough. Bore 158 receives wrist pin 159. The wrist pin and coil spring both serve to maintain glide ring 156 in a radially outward position so as to bear against the cylinder wall.

The two-part piston assembly of the present invention contains bottom connecting rod 160 as shown in FIG. 10.

The connecting rod contains a top bore 161 through which wrist pin 159 extends. Bottom bore 163 of the connecting rod extends about and matingly engages an appropriate portion of the crankshaft. In order to permit rotation of connecting rod 160 about the crankshaft 130, sealed portion 164 of the connecting rod contains bearings therein.

The net result of the two-part piston ring assembly of the present invention is that bearing 164 of connecting rod 160 can freely rotate with the crankshaft in a rotary or circular motion whereas top bore 161 moves in only a linear or reciprocal motion allowing piston rod 148 with the piston head and base thereon to move only in a linear reciprocating direction. The same thus prevents lateral forces from being applied to the cylinder wall which often results in wear and can create an oval-shaped cylinder wall. The two-part piston ring assembly of the present invention thus promotes long life of the piston and cylinder wall.

Although each piston serves to compress the gas admitted therein to a higher pressure, a desirable aspect of the present invention, as noted above, is that each subsequent piston head has a smaller area. For example, piston #1 (131) can have a diameter of approximately 1¾ inches, whereas piston #2 has a diameter of approximately 1¼ inches, and piston #3 can have a diameter of approximately ½ inch, which can be the diameter of essentially piston rod 148. Desirably, the increase in pressure from each stage or piston is proportional to the others. The compression ratio of each piston can vary, but generally is the same. Although compression ratios of up to 10 can be utilized, the desirable pressure range is from approximately 6 to about 8.

Inasmuch as heat is built-up during compression of the oxygen-enriched gas, the flow lines between the pistons can be extended so that they are long enough to permit the heat of compression to be absorbed by ambient air and thus cool the enriched pressurized gas therein. As shown in FIG. 8, cooling line 182 from the first piston to the second piston can be in the form of an undulating path or the like and the same is true with regard to cooling line 184 between the second and third pistons.

The operation of the compressor portion of the apparatus is as follows. Electric motor 105 which operates independently of the compressor feeding air to the molecular sieves in the oxygen concentrator portion of the apparatus, through drive belts 109 and 122, rotates crankshaft 130 thereby causing piston #1, #2, and #3 (131, 133, 135) to reciprocate and compress air in their respective chambers. More specifically, enriched oxygen gas from the compressor buffer tank is fed to the first piston. Piston 131 contains an inlet check valve 172, which permits air to enter the cylinder head space above the piston, and outlet check valve 173, which permits the compressed gas to exit from the first piston. The check valves permit flow of the gas in one direction so that once the gas is admitted to the first piston, during the compression stroke thereof it cannot be forced back out to the buffer tank. Similarly, once forced out of the first piston, outlet check valve 173 prevents the gas from being sucked in during the intake stroke of the first piston. In a similar manner, second piston 133 has an inlet check valve 175 which permits the compressed air from piston #1 to be drawn into the head space above piston 133, but prevents it from being forced back into the first piston. Outlet check valve 176 prevents the gas compressing the second piston from being drawn back into the piston once it has been expelled therefrom. In a similar manner, the gas which has been further compressed in piston #2 is fed into piston #3 (135) through inlet check valve 178 where it is further compressed. The compressed gas is then fed through outlet check valve 179 into enriched oxygen gas storage cylinder 500. Outlet check valve 179 thus prevents the highly compressed stored gas in the cylinder from being admitted back into the third piston.

During the operation of the compressor, the gas in portable cylinder 500 which is initially at ambient pressure, is gradually built up to desired pressure. One such suitable pressure is approximately 2,250 psi. Of course, different cylinders can accept either higher or lower gas pressures and readily maintain the same. Rupture disk 180 is a safety feature designed to rupture at a pressure in excess of the desired storage pressure of the gas cylinder. Thus, in the present embodiment, such a pressure can be approximately 2,800 psi. Although not shown, rupture disks can also be provided in the flow lines from the exit of the first and second cylinders to prevent undue build-up in these lines. A pressure regulator 181 serves to emit the oxygen-enriched gas at a pressure of about 5 psi to a patient via a flow meter (not shown) at any desired rate, such as from about 0.1 to about 6 liters per minute.

As previously noted, the buffer tank contains oxygen-enriched gas at a pressure of generally from about 7 or 14 psi to about 21 psi. The compressor is designed to commence compression generally when the pressure in the tank is generally at a maximum until it drops to a predetermined pressure, e.g., 7 or 8 psi. In general, the pressure is electrically controlled by various switches, sensors, relays and the like. Briefly, a master ON/OFF switch emits power to compressor motor 105 which in turn causes the crankshaft to rotate and compress air. Two pressure-sensitive switches exist: a low pressure sensor which detects pressure below a predetermined value, e.g., 7 to 12 psi, and a high pressure sensor which detects pressure above 2,250 psi. When the low pressure sensor detects pressure below the predetermined level, it will turn off motor 105 through a relay switch. This allows oxygen inflow from the concentrator to be built-up in the buffer tank to a desired pressure. The low pressure sensor is a solid-state relay. Should the relay fail, it will fail closed and allow the motor to continue to run. Accordingly, this relay switch is connected in series with the high pressure sensor mechanical relay switch which will shut the motor off when the pressure in the cylinder reaches approximately 2,250 psi.

FIGS. 5 and 6 show the electrical circuitry of the compressor. Power is fed to the compressor initially through the resettable breaker 600 and then to power switch 610. When the power switch is pushed to the "ON" position, power passes to the motor start switch 620, the start relay common contacts 630, and also lights the power indicator 640. When start switch is depressed, the start relay coil is energized which causes both switches of the relay to close.

One of these closed switches passes the power to high pressure switch 650 which is normally closed when the output pressure of the compressor is under 2,250 psi. The output of the high pressure switch is fed back to the start relay coil to keep the coil energized without the start switch being depressed, but will cut power to the coil when high pressure is reached. (This occurs when a tank has been filled.) The output of the high pressure switch is also connected to the common of low pressure switch 660. While the input pressure from the concentrator is above the predetermined value, e.g., 7 psi, the low pressure switch is closed and the normally closed contact has power. This power signal is fed to the drive contact of the solid-state relay which, in turn, allows the solid-state output to be "turned on." The output of the high-pressure switch is also connected to the run indicator 670 which then lights up.

The second closed switch of the start relay is connected to the "input" of the solid-state relay. When the solid-state relay is turned on by the signal from the low pressure switch, power is passed to motor 105 and its start capacitors through the solid-state output. A common line is connected to the other side of the motor to complete the circuit. An hour meter 690 is wired in parallel to the motor to monitor motor run time.

When the above occurs, the motor beings to run and remains running until one of two conditions occur. The first condition would be the input pressure to the compressor falls below a predetermined value, e.g., 7 psi. This will cause low pressure switch 660 to open and solid-state relay 695 to turn off, which in turn shuts off motor 105. If the input pressure to the compressor rises above a desired predetermined pressure, low pressure switch 660 will close and once again turn on the solid-state relay and start the motor. This is a normal occurrence that is dependent upon concentrator efficiency and may be repetitive.

The second condition that will shut off the motor occurs when an oxygen tank has been filled. The output pressure will rise above 2,250 psi and therefore cause high pressure switch 650 to open. This cuts the power to the start relay coil which causes both switches to open and cuts the power to both the input of the high pressure switch and the input to the solid-state relay thereby shutting off the motor. To start the motor after this condition is reached requires start switch 620 to be depressed. If greater than 2,250 psi remains, the high pressure switch will remain open and no signal will be fed back to the start relay coil to keep it energized therefore causing the motor to remain off. While the high pressure switch is open, run indicator 670 remains off.

Any direct shorts between power and common or any condition that draws more than 8 amps of current will cause resettable breaker 600 to pop open.

As apparent from the above, the operation of compressor 100 is completely independent of the oxygen concentrator as well as utilization of gas compressed thereby as a power or energy source for the compressor. In other words, the pressure accumulated in the oxygen concentrator is not utilized to drive or operate a pressure intensifier.

A distinct advantage of the apparatus and method for forming oxygen-enriched gas and compression thereof according to the present invention is the creation of a mobile or portable source of gas containing high purity oxygen. Patients who require oxygen-enriched gas, as from about 80 to about 98 percent, are no longer confined to the vicinity of an oxygen concentrator as for example a bed, home, hospital, or a wheelchair. Rather, the patient can carry the mobile gas cylinder in any convenient manner, such as in a backpack, and thus can take trips via wheelchair, an automobile, and even planes and trains. Depending upon the pressure and size of the storage cylinder, the oxygen supply can be anywhere from about 2 to about 24 hours or even longer.

RADIAL COMPRESSOR

A further embodiment of the present invention relates to an electro-mechanical oxygen distribution device or system as for use in a home to supply a patient with concentrated oxygen and also to concurrently supply pressurized and concentrated oxygen to a storage cylinder as for a patient's personal ambulatory use. The device is designed to be utilized in association with an oxygen source capable of supplying oxygen at a preferred concentration of at least 85% or 90% by volume at various pressures such as generally from about 2 to about 20 psig, and desirably from about 2.5 or about 4 to about 10 psig. Sources of concentrated oxygen include an oxygen concentrator as set forth herein above, or, conventional or commercially available oxygen concentrators, such as for example, but not limited to, Mallinckrodt-Aeris 590; Russ Products—Millienum; Sunrise; and the like. Such concentrators can have various oxygen concentration outputs, pressures, and a desirable flow rates such as at least about 3, 5 or 6 liters per minute.

The oxygen distribution system or device 800 has housing 810 as well as oxygen test mode inlet 815, oxygen normal operation inlet 820 for receiving oxygen from a concentrated oxygen source, oxygen outlet 825 for feeding oxygen to a patient, oxygen flow meter 830 for regulating the flow of oxygen to a patient, pressure gauge 835, power switch 840 for turning the compressor unit or device on and off, and fill connector 845 for connecting the compressed gas to gas storage cylinder 1000.

Figure 11:
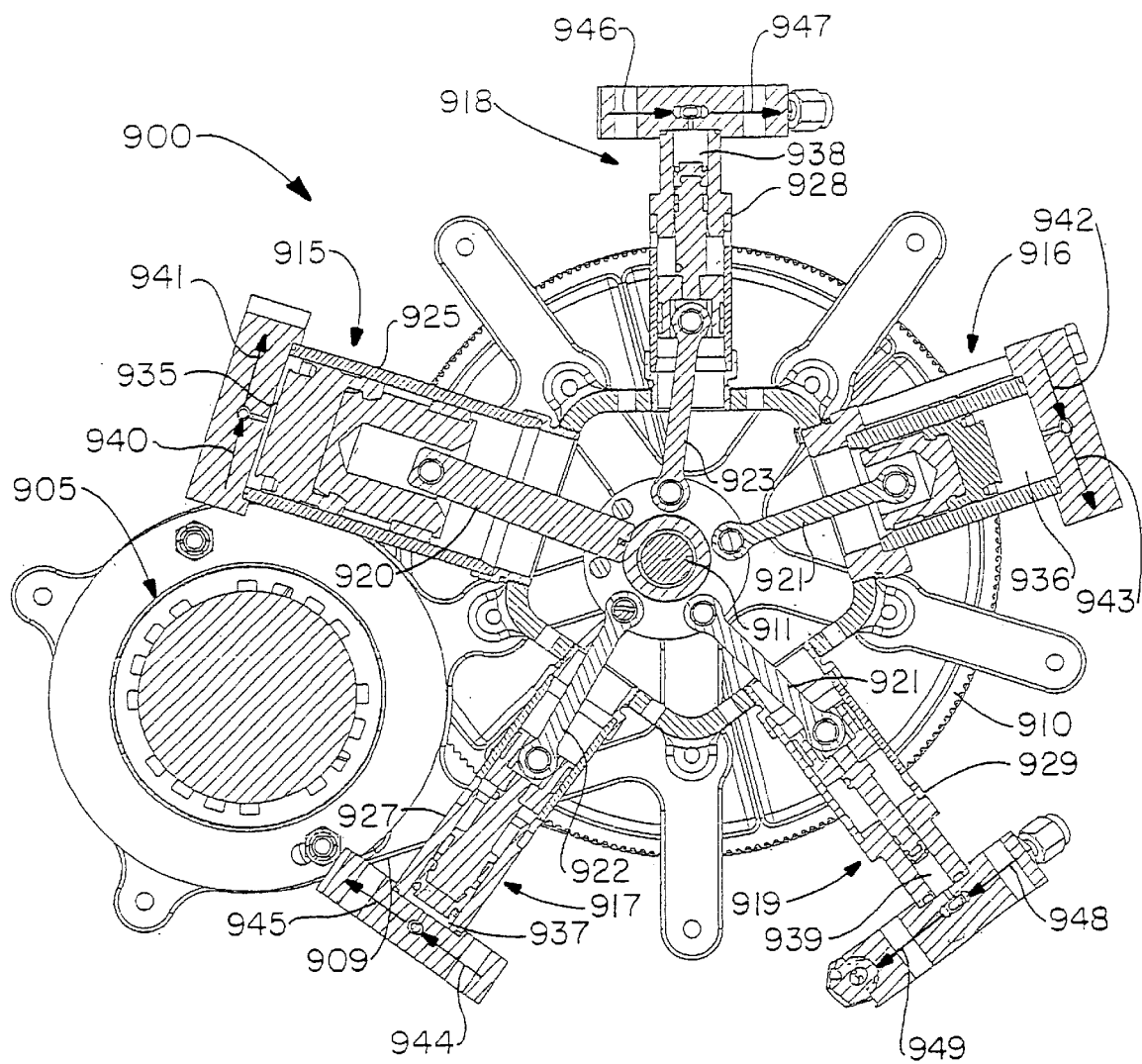
FIG. 11 is a top plan view of a radial compressor of the present invention.
Figure 12:
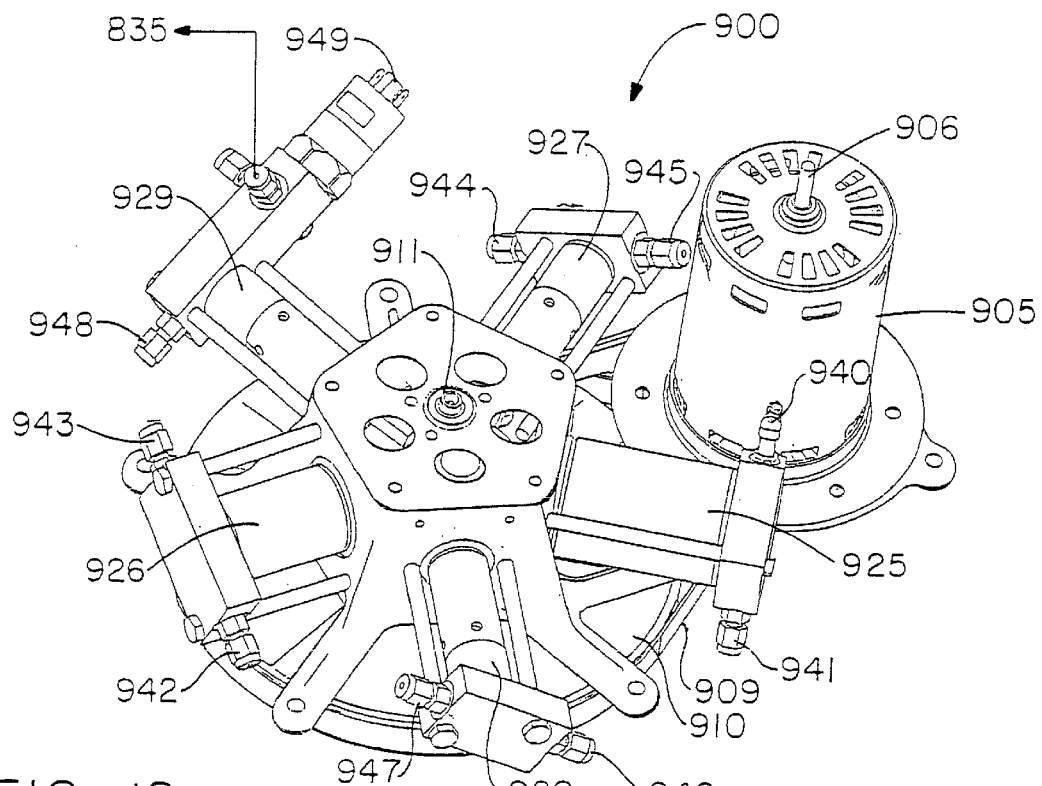
FIG. 12 is a perspective view of the radial compressor of FIG. 11 showing inlet and outlet connections of the compression cylinders.
Figure 13:
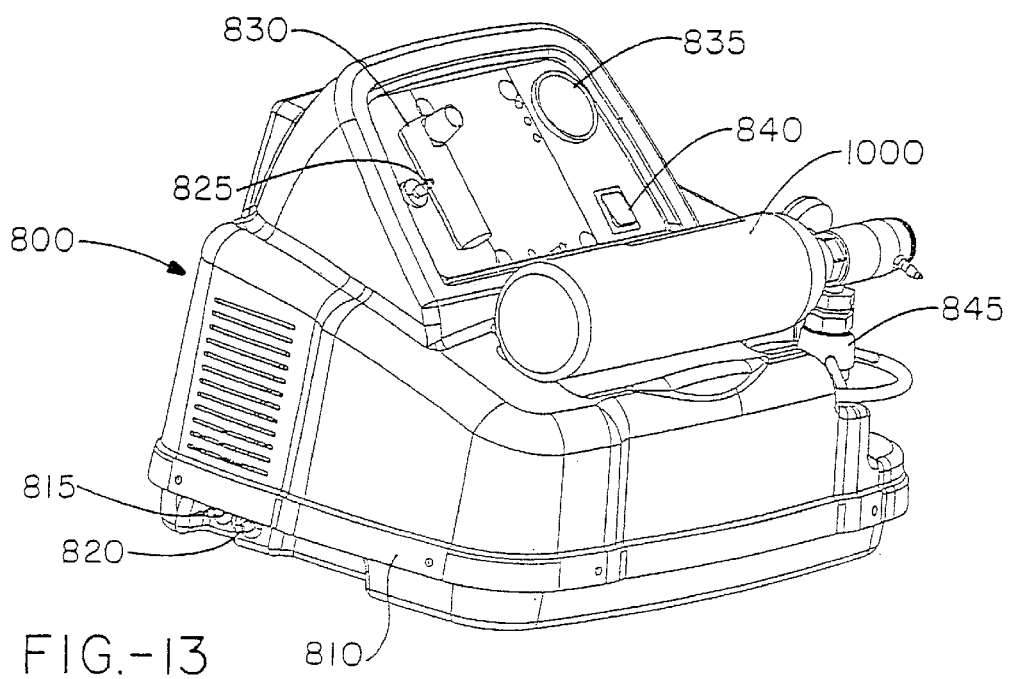
FIG. 13 is a perspective view of the portable high pressure oxygen conserving device of the present invention.

Considering the radial compressor, as seen in FIGS. 11 and 12 the radial compressor generally utilizes an AC electric drive motor 905 which can rotate at any desired speed, such as generally from about 500 or 1,000 to about 3,600 or 6,000 RPM, and preferably from about 1,100 to about 1,300 RPM. Generally, the drive motor can be of any horsepower and is desirably from about $1/100$ to about $1/2$ horsepower, with $1/12$ horsepower most preferred. Drive motor 905 can contain a fan (not shown) within the motor housing or immediately adjacent thereto to draw air through the motor thereby cooling the same. Power is conveyed from the motor through motor shaft 906 to drive wheel, not shown, which desirably has a variety of grooves and/or teeth therein to receive a belt such as drive belt 909. The drive belt can generally be of any suitable composition, such as rubber or reinforced rubber which provides a long service life. Drive belt 909 is connected to compressor pulley 910 which has a plurality of grooves and/or teeth therein. Optionally, an idler arm (not shown) can be utilized to keep tension on the drive belt. Compressor pulley 910 is connected to crankshaft 911. Although the present invention is only shown with a single reduction, it is conceivable to add more pulleys and reducing gearing. The single reduction utilized by the present invention is lighter and more compact and contains fewer parts than an assembly utilizing more than one reduction.

The radial multi-stage compressor of the present invention can have any number of pistons, such as from 2 to about 12, desirably from about 3 to about 8 or 10, with about 5 being preferred. As shown in FIGS. 11 and 12, the preferred embodiment contains 5 pistons 915, 916, 917, 918, and 919, that is the first through fifth pistons respectively, radially arranged around crankshaft 911. Each piston is located within separate cylinders 925, 926, 927, 928, and 929 with first piston 915 located in first cylinder 925, etc. As can be seen in FIG. 11, the pistons and cylinders or various portions thereof, have different shapes, and sizes, such as diameters, and lengths, in order to facilitate the gradual or step-wise build-up of pressures from the first cylinder through the last or fifth cylinder. For example, first piston 915 and second piston 916 have a top and base which are integrally formed from a single element, and generally have the same diameter. The third piston 917, fourth piston 918, and fifth piston 919, each have top portions which are smaller than the base portions thereof. Inasmuch as each subsequent piston is located on essentially the opposite side of the housing, the forces exerted on the various pistons by the crankshaft and the expanding air in the cylinders are generally balanced and result in the efficient transfer of energy. Moreover, the radial design results in a lightweight housing, which can be made of aluminum.

The radial compressor is designed so that the volume of gas is reduced, desirably proportionally, in each succeeding piston/cylinder assembly. Thus, as can be seen in FIG. 11, the compressible area 935 of the first piston/cylinder assembly is larger than the compressible area 936 of the second piston/cylinder assembly, and so on. The compression ratio can generally range from about 1 to about 10, and is preferably from about 2 to about 5, with about 2.5 being most preferred. Motor 905 drives annular crankshaft 911 which drives master connecting rod 920, as well as slave connecting rods 921 through 924 each operably connected thereto. The crankshaft has an offset thereon to allow reciprocation of the pistons.

The operation of the radial compressor generally is as follows: Drive motor 905 through, drive belt 909, and pulley 910 rotates crankshaft 911 and thus operably causes first through fifth pistons 915–919 to reciprocate and compress a source gas in their respective chambers. More specifically, a gas, which is preferably enriched oxygen gas is fed to the first piston 915. The gases which are fed or supplied to the radial compressor can be supplied from various sources, herein incorporated by reference, such as molecular sieve oxygen concentrator, a product tank or a buffer tank. Alternatively, gases from liquid or a high pressure oxygen cylinder which is typically too large and heavy to be easily moved, can serve as a source gas which is fed to the compressor. These large cylinders contain a wide range of oxygen therein, such as typically from about 800 to about 900 cubic feet of compressed or liquified oxygen therein.

The piston/cylinder assemblies in each cylinder head contain conventional check valve members such as ball and spring assemblies such as those set forth in FIG. 8 which permit a gas to flow in and out of the piston/cylinder assembly in a desired fashion, i.e. one direction. The preferred check valve member of the present embodiment has a spring rated preferably at 2 psi or less. In order to ensure the compressed concentrated oxygen does not flow from a subsequent compression cylinder back into a prior cylinder, each cylinder head assembly will contain two outlet check valves located sequentially with respect to one another as diagramically shown in FIG. 14.

FIGS. 11 and 12 show various fittings and piston head assemblies containing check valves. Inlet check valve 940 of the first piston assembly permits the gas to enter first compressible area 935 and outlet check valves 941 permits the compressed gas to exit the first piston. The check valves permit the flow of gas in one direction so that once the gas is admitted to the first piston, it cannot be forced back out through the inlet check valve during the compression stroke of the piston. Similarly, once forced out of the first piston, outlet check valves 941 prevents gas form being sucked in during the intake stroke of the first piston. In a similar manner, second piston 916 has an inlet check valve 942 which permits the compressed gas from the first piston/cylinder assembly to be drawn into the second compressible area 936, but prevents it from being forced back into the first piston. Outlet check valves 943 prevents the gas compressed in the second piston/cylinder assembly from being drawn back into the same once it has been expelled therefrom.

In yet a similar manner, third piston 917 has an inlet check valve 944 which permits the compressed gas from the second piston/cylinder assembly to be drawn into the third compressible area 937, but prevents it from being forced back into the second piston. Outlet check valves 945 prevents the gas compressed in the third piston/cylinder assembly from being drawn back into the same once it has been expelled therefrom.

In a similar manner, fourth piston 918 has an inlet check valve 946 which permits the compressed gas from the third piston/cylinder assembly to be drawn into the fourth compressible area 938, but prevents it from being forced back into the third piston. Outlet check valves 947 prevents the gas compressed in the fourth piston/cylinder assembly from being drawn back into the same once it has been expelled therefrom.

Figure 14:
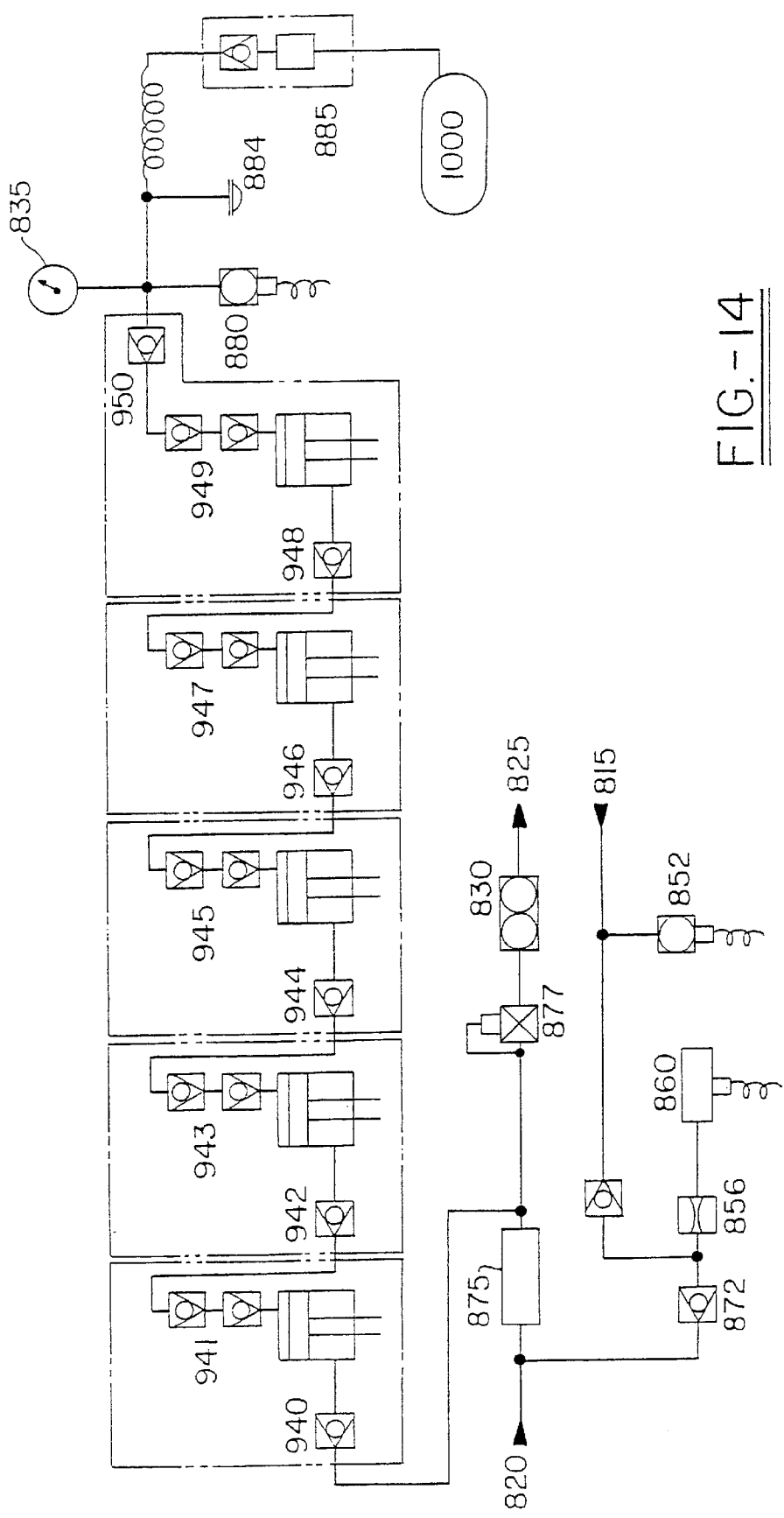
FIG. 14 is a mechanical and quasi-electrical schematic of the radial compressor and the flow system of the present invention.

Finally, in a similar manner, fifth piston 919 has an inlet check valve 948 which permits the compressed gas from the fourth piston/cylinder assembly to be drawn into the fifth compressible area 939, but prevents it from being forced back into the fourth piston. Outlet check valves 949 prevents the gas compressed in the fifth piston/cylinder assembly from being drawn back into the same once it has been expelled therefrom. As shown in FIG. 14, appropriate tubing able to withstand high pressures such as metal tubing, connects various parts of the oxygen distribution device such as the various piston/cylinder assemblies, the buffer tank, the various regulators, the storage cylinder, etc., in a conventional manner known to those skilled in the art.

As shown in FIG. 11, each sequential piston cylinder assembly is not located adjacent to the next higher pressurizing piston cylinder assembly in a circumferential direction around the compressor, but is staggered or offset from one another by at least one piston cylinder assembly so as to balance the forces on the compressor and the crankshaft. In other words, each succeeding piston cylinder assembly with respect to increasing the pressure of the enriched oxygen from the previous assembly is located at least two assembly positions away in a circumferential direction so that there is desirably at least one intervening piston cylinder assembly between each set or pair of sequentially or succeeding pressure piston cylinder assemblies.

As concentrated oxygen is fed to the radial compressor, the first cylinder will gradually build up a pressure, with the second cylinder gradually building up a higher pressure, etc. until a desirable pressure is reached in storage cylinder 1000. While the ranges in each cylinder can vary widely, the desired range from the concentrator or other oxygen source as from about 2 to about 20 psig is approximately 34 psig. The second compressor will gradually build up to a pressure of approximately 110 psig with a third compressor gradually building up to a pressure of approximately 300 psig. The fourth compressor will gradually build up to a maximum pressure of about 800 psig whereas the last or fifth compressor will build up to a maximum pressure of approximately 2,000 psig. The above pressures are generally relative for a desired pressure of about 2,000 psig and of course will vary proportionally for a five stage compressor with regard to any other desired end pressure such as about 1,500 psig, 2,500 psig, 3,000 psig, etc. Generally, cylinder 1000 can accept pressures in a range generally from about 500 to about 4,000 psig, desirably from about 1,500 psig to about 3,000 psig, and preferably from about 1,900 psig to about 2,100 psig.

The compressed gas is then fed through connector check valve 950 into a gas storage cylinder 1000 through appropriate tubing, connectors, valves, and the like. These storage cylinders can generally be of any conventional size with standard sizes such as M6, C, D, and E, being suitable. Typically, the gas cylinder can hold a volume of compressed gas in a range generally from about 10 to about 650, desirably from about 50 or 100 to about 400 or 500, and preferably from about 150 to about 250 liters. Desirably, the cylinder has a built in pressure gauge of from about 0 to about 3,000 psig, and is equipped with a self-contained release valve as well as a high pressure rupture disk set for any desirable pressure such as about 6,000 psig. It can also have a hose barb outlet for connection to a patient cannula.

As stated above, the radial compressor 900 can be substituted directly for compressor assembly 100, that is in association with an oxygen concentrator, and with various flow schemes, designs, etc., whether preferably prioritized to insure that a patient receives a required amount of oxygen-enriched gas, or not prioritized. Accordingly, the flow diagram of FIGS. 2, 3, or 4 can be utilized but it is to be understood that generally any other flow system can also be utilized to route the enriched oxygen from product tank 30 either directly or indirectly, etc., to radial compressor 900.

The oxygen distribution system or device of the present invention containing the radial compressor is diagrammically shown in FIG. 14. The oxygen distribution device generally comprises oxygen sensor 860, reservoir or buffer tank 875, to accumulate or store the concentrated oxygen, the radial multi-stage compressor 900, high pressure switch 880, pressure gauge 835, output oxygen fitting or connector 845, portable high pressure cylinder 1000. Also included is flow regulator 877 and flow meter 830. As apparent from FIG. 14, the oxygen device also contains a test mode aspect, explained in greater detail hereinbelow, to determine at least the concentration of the oxygen from an oxygen concentrator, a large oxygen cylinder, or other source, before it is connected to the oxygen device. While oxygen distribution device 800 is assigned primarily for home use, it can also be used in other institutions such as nursing homes, clinics, hospital rooms, offices, and the like. As noted, the oxygen distribution device can receive various levels of concentration of oxygen such as at least about 50% or 75%, and desirably at least about 80%. However, with respect to the present invention, the oxygen device is generally designed to receive at least about 85%, and preferably at least about 90% oxygen and more preferably about 93% by volume plus or minus 3%.

Once the level of oxygen concentration from the oxygen concentrator, etc., has been determined by the test mode system to meet the predetermined, minimum requirement or level, the oxygen source such as a concentrator is attached to oxygen inlet 820. From there a small portion is fed to oxygen sensor 860 which continuously monitors the oxygen concentration. The remaining great majority of the oxygen is fed to a reservoir or buffer tank 875 whereafter it is channeled into two flow streams with a selected or predetermined portion of oxygen such as from about 1 to about 3, 4, or 5 and preferably about 2 liters per minute being fed to the compressor and with a selected or predetermined portion such as from about 0.1 to about 6, desirably from 1 to about 0.5 to about 5, and preferably from about 1 to about 3 liters per minute, flowing to a patient. These two portions naturally add up to the total amount or flow of oxygen from the reservoir of buffer tank 875; that is one flow stream such as that to the patient is the difference of the flow stream going to the compressor based upon the total flow or amount of oxygen exiting from the buffer tank. The oxygen distribution system of the present invention is prioritized in that the radial compressor will only run when oxygen sensor 860 determines that the oxygen concentration is at or above a minimum predetermined level, for example 90% by volume. Thus, should the oxygen concentration drop below the predetermined level during operation of the compressor, sensor 960 will shut off the compressor until the concentration reaches the predetermined level. However, while the compressor is shutoff to build up the oxygen level, the enriched oxygen is continuously fed to the patient. As apparent from FIG. 14, the enriched oxygen from the buffer tank passes through pressure regulator 877 and flow meter 830. Pressure regulator 877 is set at any desired predetermined pressure level such as anywhere from about 1 to about 5 and desirably about 3 psig. The flow meter can be set by the patient, or by any other competent medical person such as a physical therapist, medical doctor, etc. to a desired flow rate.

The oxygen being fed to the compressor, as previously indicated, goes through a series of compression stages or cylinders with each subsequent stage pressurizing the gas to a higher pressure until finally the last stage achieves the desired indicated pressure whereupon cylinder pressure switch 880 will turn off compressor motor 905. As a safety backup, burst disk 884 is provided to prevent an undue buildup of pressure within the storage cylinder.

Generally, the only requirement required by the patient in operating the oxygen distribution device of the present invention is to turn on power switch 840 and to set flow meter to desired rate as determined by a medical person or the like.

Referring to FIG. 14, the device 800 may also advantageously include an oxygen concentration testing function. This test mode system includes the test mode inlet 815. The inlet 815 communicates with the oxygen sensor 860 through a check valve 854 whose downstream side is in communication with the downstream side of a check valve 872 that normally passes gas from the normal mode inlet 820. The downstream sides of the check valves 854, 872 are both in communication with a flow restrictor 856 which limits the flow of gas to the oxygen sensor 860. The check valve 872 prevents the flow of gas from the test mode inlet 815 toward the normal mode inlet 820. The check valve 854 prevents the flow of gas from the normal mode inlet 820 toward the test mode inlet 815.

A test pressure switch 852 senses the pressure of gas applied to the test mode inlet 815. The switch 852 provides an indication that pressurized gas is being applied to the test mode inlet 815. The switch 852 may, for example, be actuated by a gas pressure of 2.1 psi or greater.

Upon indication of pressurized gas being applied to the test mode inlet 815, the compressor 900 is disabled and the oxygen sensor 860 is then used to test the oxygen level or concentration of the gas applied to the test mode inlet 815.

Figure 15:
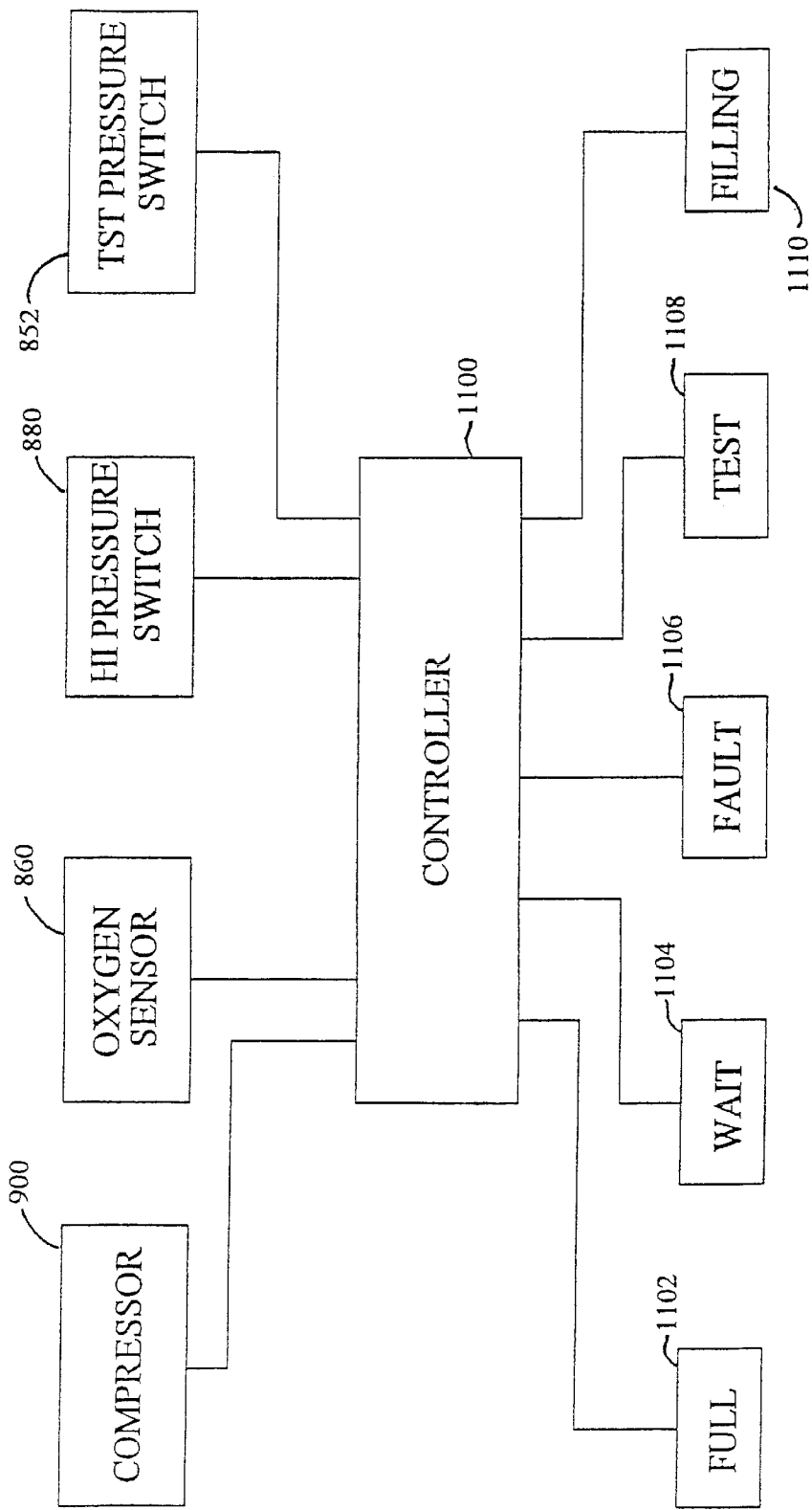
FIG. 15 is a block diagram of the electrical circuitry of the invention including an oxygen concentration test mode aspect.

Referring to FIG. 15, the operation of the device 800 may, for example, be advantageously controlled by a controller 1100. The controller 1100 is most preferably a microcontroller, but may be, for example, a microprocessor with associated memory and input/output circuitry, an application specific integrated circuit, a field programmable gate array, or other suitable programmable device.

The controller 1100 receives inputs from the oxygen sensor 860, the high pressure switch 880 and the test pressure switch 852 and provides outputs to the compressor 900 and the indicators 1102, 1104, 1106, 1108, 1110. The controller 1100 may also, for example, incorporate the previously mentioned control means 50. The indicators 1102, 1104, 1106, 1108, 1110 may be, for example LEDs, light bulbs, an LCD screen, or other suitable indicators, including, for example, audible indicators.

When the power switch 840 is first turned on, the FULL indicator 1102, the WAIT indicator 1104, the FAULT indicator 1106 and the TEST indicator 1108 will come on for a short time (e.g., 1 second) to provide an indication that these indicators are functioning. Then the indicators 1102, 1106, 1008 will go off.

The WAIT indicator 1104 will remain on long enough for the oxygen sensor 860 to reach operating temperature (e.g., 3.0 minutes).

The controller 1100 also monitors the heater current and voltage and the output current voltage of the oxygen sensor 860 whenever the device 800 is turned on. If a fault in the oxygen sensor 860 is detected at any time, the WAIT indicator 1104 is flashed at a one second rate, the FAULT indicator 1106 is activated and all other indicators are deactivated. In this state, the compressor 900 and the test mode function will not operate.

If no gas pressure is detected by the test pressure switch 852, the device 800 will operate in normal mode. That is, if there is an acceptable level of oxygen as sensed by the oxygen sensor 860 in the gas applied to the normal mode inlet 820 (e.g., greater than 91 percent) the compressor 900 will run and the FILLING indicator 1110 will be activated. If the high pressure switch 880 is activated, the FULL indicator 1102 will be activated, the FILLING indicator 1110 will be deactivated and the compressor 900 will be deactivated by the controller 1100.

If the high pressure switch 880 is activated during the warm up period (e.g., a full bottle (e.g., 2,000 psi) already attached to the oxygen outlet 825), the FAULT indictor 1106 will be flashed at a one second rate by the controller 1100 and the device 800 must be reset to operate.

If the test pressure switch 852 detects gas pressure at the test mode inlet 815, the device 800 will operate in test mode. If the gas pressure at the inlet 815 is removed, the device 800 will again operate in normal mode.

Whenever the device 800 enters or leaves test mode, the controller 1100 will suspend the operation of the device 1100 for a period of time (e.g., 30 seconds) and activate the WAIT indicator 1104 to allow the oxygen sensor 860 time to stabilize with a new input gas.

In test mode, the controller 1100 will disable the compressor 900, activate the TEST indicator 1108 and use the oxygen sensor 860 to test the oxygen level of the gas applied to the test mode inlet 815. If there is an acceptable level of oxygen, the controller 1100 will activate the FULL indicator 1102. Otherwise, the controller 1100 will activate the FAULT indicator 1106.

The test mode of operation permits a user to conveniently check the oxygen content of a cylinder or concentrator output without activating the compressor of the device. The user activates the test mode by merely connecting a gas source to the test mode inlet. Normal operation resumes when the gas source is removed. The user is not required to perform any other operation. This is particularly advantageous for impaired, unsophisticated or technology intimidated users.

The radial compressor and assembly comprising connecting tubing etc. is compact and light, approximately ¼ the size of compressor assembly 100 shown in FIG. 8, and approximately ¼ the weight thereof. Advantageously, the radial compressor of the present invention can be utilized with any commercially available oxygen concentrator and has a unitized construction and compact design for easy placement and storage. The radial compressor of the present invention is very efficient with respect to power consumption, is quiet when running, and produces very little vibration. Moreover, while the consumption of power is low, the unit has generally the same features as other units such as in FIGS. 1–10, for example, the same fill time.

Figure 16:
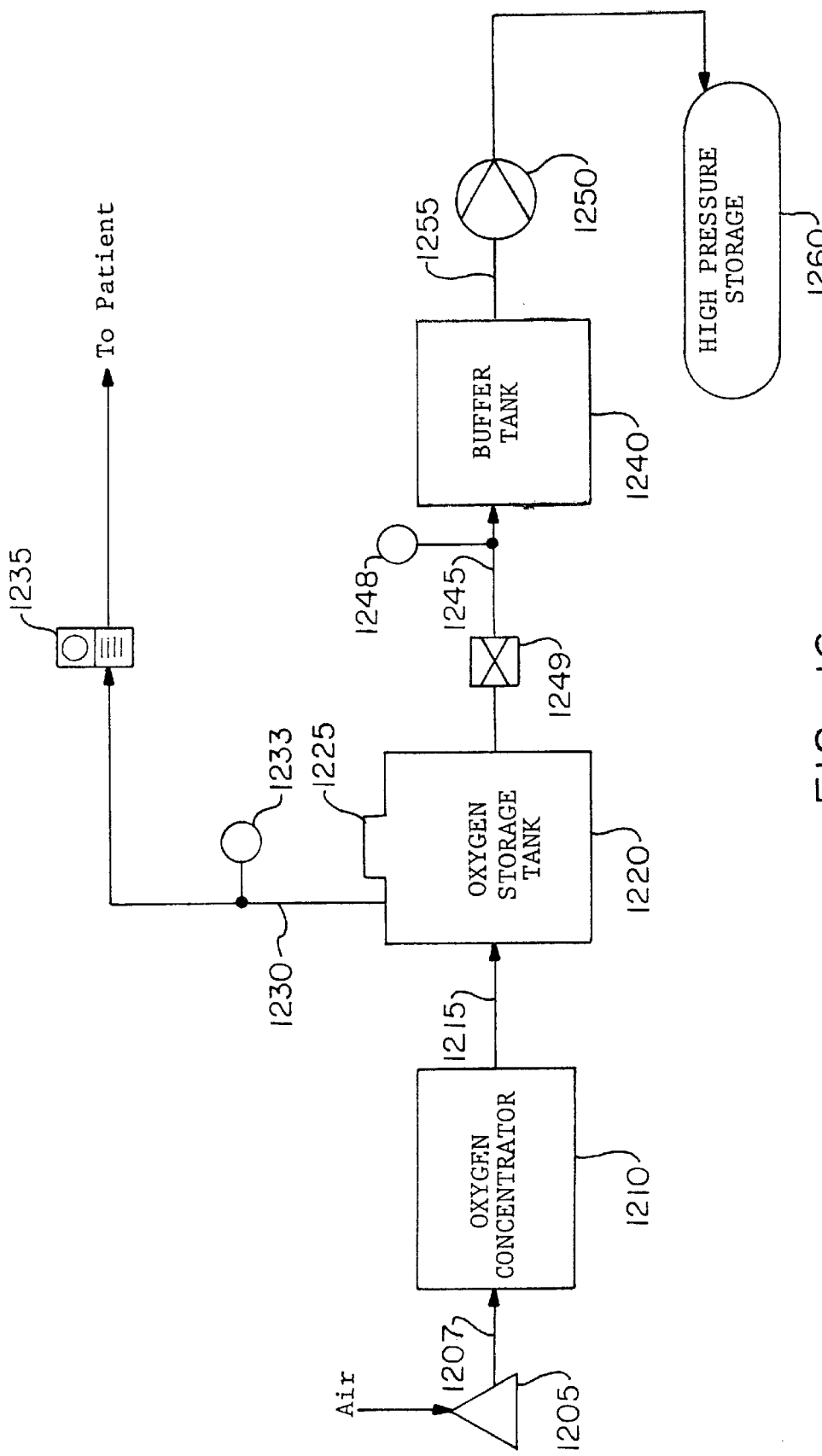
FIG. 16 is a block diagram of the apparatus and process of the preferred embodiment showing the general flow at different pressures of oxygen-enriched gas from an oxygen or product storage tank to a patient as well as to eventually a compressor for compression and delivery to a high pressure, portable, storage cylinder.
Figure 17:
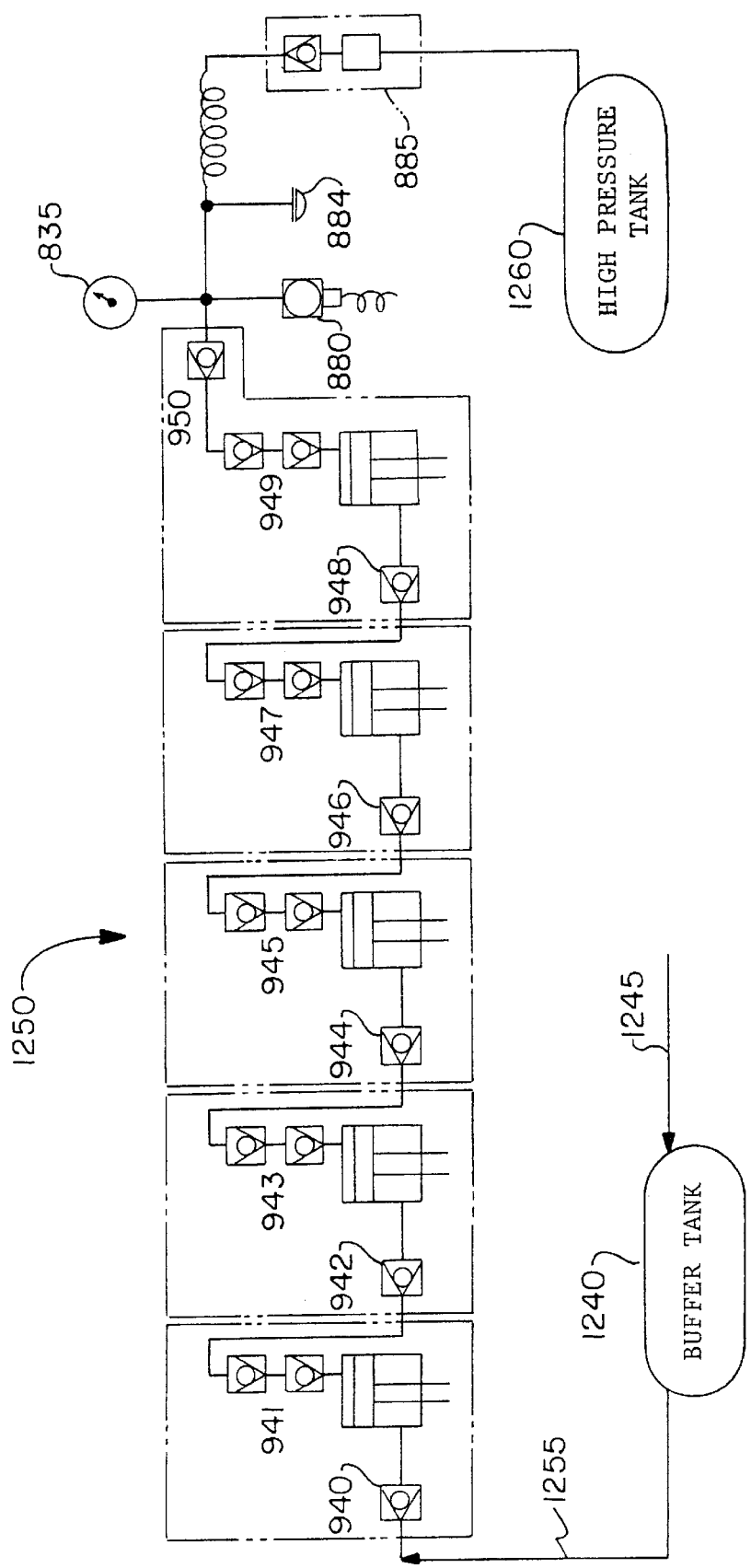
FIG. 17 is a detailed view of the embodiment shown in FIG. 16, including a buffer tank, compressor and high pressure cylinder.
Figure 18:
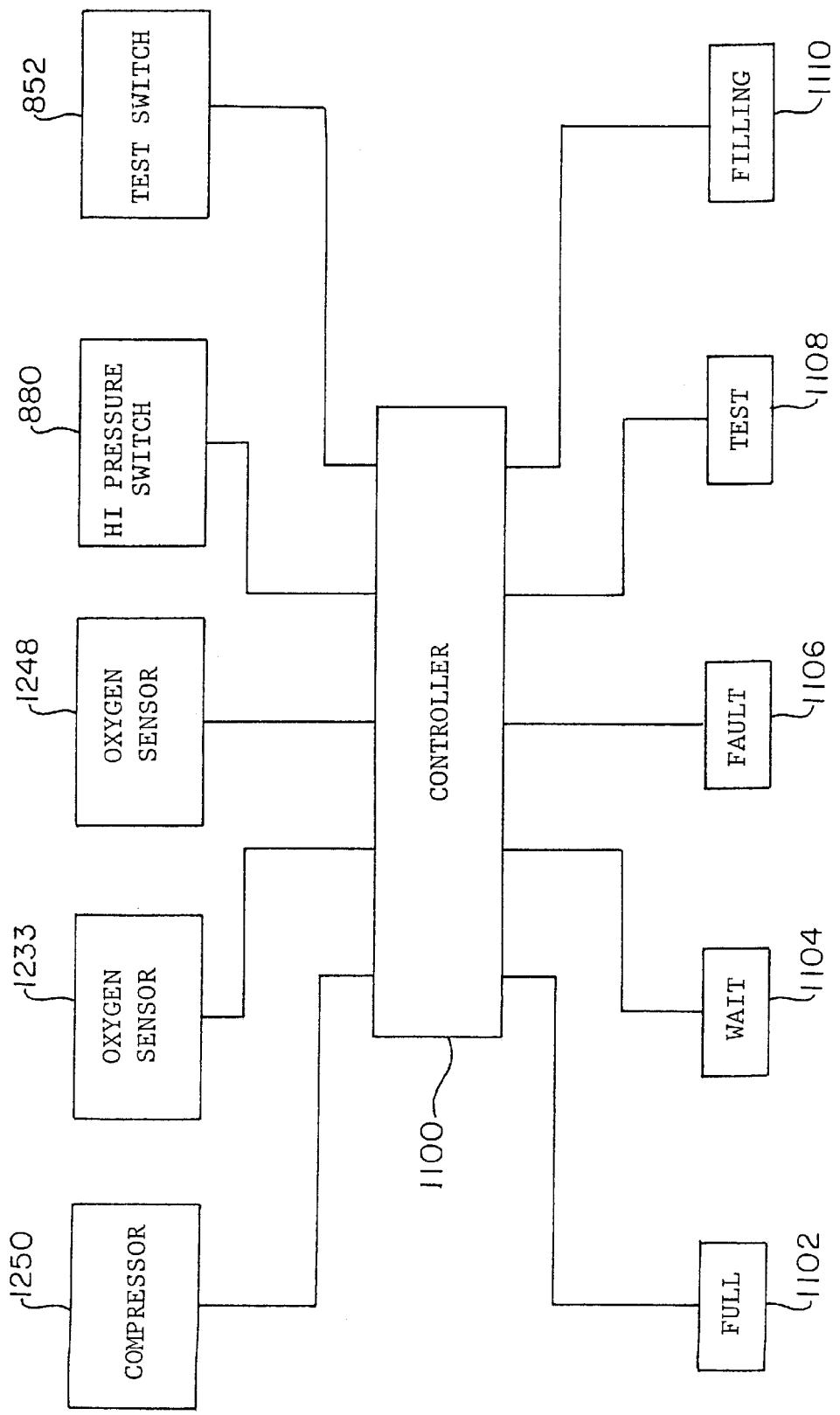
FIG. 18 is a detailed view of the embodiment shown in FIG. 16, including a controller apparatus.

Another embodiment of the present invention, similar to that shown in FIGS. 11 through 15, is set forth in FIGS. 16, 17, and 18 which feeds enriched oxygen primarily to a patient and secondarily to a buffer tank and then to a radial compressor. Unless specififed hereinbelow, the embodiments of FIGS. 16, 17, and 18 are generally the same as that set forth in FIGS. 11 through 15 as described hereinabove and hereby fully incorporated by reference. It is also to be understood that all pressures in this specification relate to pressures above atmosphere pressure, that is 5 psi is 5 pounds per square inch gauge. In the embodiment of FIGS. 16 through 18, enriched oxygen from an oxygen or product storage tank is fed through two different outlets or lines, one line directed to the patient and the other line connected to a buffer tank. The buffer tank flow line contains oxygen-enriched gas at a pressure generally that of the storage tank whereas the patient flow line feeds the oxygen-enriched gas at a reduced, low pressure to the patient. The apparatus utilizes two different and independent compressors, an initial compressor for compressing air and feeding it to molecular sieves for enriching or concentrating to a high amount of oxygen by volume and a second compressor, which operates independently of the first, for compressing the oxygen-enriched gas to a very high pressure for delivery to a high pressure storage cylinder. That is, the second, e.g. a radial, compressor is operated by a power source, e.g. a motor, engine, other than by the oxygen enriched gas as compresses by the first compressor (such as in a pressure intensifier). As with the previous embodiments, the embodiment of FIGS. 16 through 18 prioritizes the oxygen-enriched gas so that flow is always continuous to the patient and optional to the buffer tank.

A description of the apparatus for compressing and storing an oxygen-enriched gas is as follows. Initial or concentrator compressor 1205 receives air from the atmosphere and through flow line 1207 feeds it to oxygen concentrator 1210. The concentrator can be any conventional or standard concentrator known to the art and to the literature, or as described hereinabove. Such a concentrator is commercially available from Invacare Corporation, Elyria, Ohio as models 5LX and 5LX02. Typically, such oxygen concentrators, through the use of molecular sieves, enriches the oxygen to a desirable level such as at least about 50% or 75%, desirably at least about 80%, and preferably at least about 85% or 90%, more preferably about 93% by volume plus or minus 3%. The oxygen-enriched gas is fed through product tank flow line 1215 to oxygen product storage tank 1220. Pressure in the storage tank is generally the same as generated by the oxygen concentrator and can vary as from about 15 to about 20 or 22 psi. Storage tank 1220 primarily acts as a holding tank for feeding the oxygen-enriched gas to the patient but also provides oxygen-enriched gas to a buffer tank which then is fed to a second independent compressor, which operates independently of the oxygen concentrator compressor, and subsequently to a high-pressure storage cylinder.

Integral with oxygen storage tank 1220, is pressure regulator 1225 which serves to reduce the oxygen-enriched gas to any desirable pressure for flow to patient flow meter 1235 through patient flow line 1230. Accordingly, the pressure regulator emits oxygen-enriched gas from the product storage tank to a first outlet such as line 1230 at a reduced or low pressure. While pressure regulator 1225 can be located on or in any portion of the storage tank, it is conveniently an integral part of the storage tank lid or cap. That is, concentrated or oxygen-enriched gas within the product storage tank before exiting the same is fed to the pressure regulator 1225 which reduces the pressure to a desirable predetermined low pressure such as from about 3 or 4 to about 10 psi with a desired pressure being about 4 to about 6 or 8 psi and preferably about 5 psi. The oxygen-enriched gas is then fed to patient flow meter 1235 where, as in the prior embodiments, it can be adjusted to any flow rate such as from about 0.1 or 1.0 to about 3, 5, or 6 liters per minute. Flow meter 1235 can be adjusted by a patient, or by a physical therapist or other medical personnel.

An oxygen sensor can be located either within oxygen concentrator 1210 or, as shown, on patient flow line 1230 as oxygen sensor 1233. When located in the oxygen concentrator, the sensor measures the level of the oxygen by volume in the gas and if it is below a predetermined range, a safety warning such as by a light, buzzer, etc. is activated warning the patient or user of the low oxygen-enriched gas value. This prevents a patient from utilizing the oxygen concentrator if the oxygen value is too low. Alternatively, when located on patient flow line 1230, the sensor also monitors the level of the oxygen in the gas to ensure that the concentration is above a predetermined value. Otherwise, a safety warning such as a light, buzzer, etc. is activated to warn the patient of low oxygen condition.

An independent or separate second outlet feeds oxygen-enriched gas from the oxygen or product storage tank to buffer tank 1240 through buffer tank flow line 1245. The pressure of the oxygen-enriched gas of the second outlet is independent of and is greater than the low pressure of the first outlet and generally is at the pressure of product storage tank 1220. Desirably, the moderate pressure in buffer flow line 1245 is from about 10, 12 or 15 to about 20 or 22 psi.

Flow restrictor 1249 located in buffer tank flow line 1245 serves to limit the flow of the oxygen-enriched gas so that a sufficient amount is generally always available for the patient and the remaining amount, which often is small, is fed solely to the buffer tank, etc. Flow line 1245 also contains an oxygen sensor 1248 which continuously monitors the concentration of the oxygen. The concentration of oxygen to the buffer tank is maintained at a predetermined level or set point, typically 93% oxygen by volume plus or minus 3%. If sensor 1248 detects a value lower than the predetermined set point, the electronics of the apparatus are designed to shut off compressor 1250. Stopping the radial compressor permits the oxygen concentrator to process air at a slower rate thus resulting in an increased oxygen concentration or purity so that the predetermined oxygen concentration such as about 93% oxygen by volume can once again be quickly achieved.

The right-hand side of FIG. 16 relating to the buffer tank, the compressor and the high pressure storage cylinder, etc. is further detailed in FIG. 17.

Buffer tank 1240 acts as a holding tank for the oxygen-enriched gas which is fed to compressor 1250 via line 1255. While compressor 1250 can be any conventional compressor as opposed to a pressure intensifier, it preferably is a radial compressor as described hereinabove and accordingly fully incorporated by reference, wherein like numbers describe like parts. Through the various stages, such as set forth above, the oxygen-enriched gas is compressed in stages until a suitable end stage emits the oxygen at a pressure for storage in high pressure storage cylinder 1260. After being compressed by the radial compressor, and once a sufficient amount of oxygen-enriched gas has been fed to high pressure storage cylinder 1260 to achieve a desired predetermined pressure, pressure switch 880 will automatically turn off compressor 1250. Pressure gauge 835 also exists as a visual indication of the amount of pressure in cylinder 1260. Check valve 885 prevents oxygen-enriched gas from flowing out of the high cylinder 1260 whenever the compressor is not being operated. As a safety backup, burst disk 884 is provided should for some reason the automatic high pressure switch 880 not turn off compressor 1250 at a predetermined high pressure level.

As noted in the prior embodiment with regard to the radial compressor setup, the pressure of high pressure storage cylinder 1260 can be any desired or predetermined pressure. While the desired pressure of cylinder 1260 is approximately 2,000 psi, it can range from about 500 to about 4,000 and desirably from about 1,500 to about 3,000 and preferably from about 1,900 to about 2,100 psi.

The advantage of the embodiment of FIGS. 16 and 17 is that independent and different pressures from the product storage tank can be utilized with the pressure component fed to the buffer tank second compressor-etc. being greater and independent of the component fed to the patient. The second or radial compressor 1250 operates independently of compressor 1205 which feeds air to the oxygen concentrator.

Referring to FIG. 18, the operation of apparatus 1200 can be operated by a controller in a manner as described hereinabove with regard to FIGS. 11 through 15. Thus, controller 1100 preferably is a microcontroller, but can be, for example, a microprocessor with associated memory and input/output circuitry, an application specific integrated circuit, a field programmable gate array, or other suitable programmable device.

Controller 1100 receives inputs from oxygen sensor 1233 or the concentrator oxygen sensor, and high pressure switch 880 and provides outputs to the compressor 1250 and the indicators 1102, 1104, 1106, 1108, 1110. The controller 1100 may also, for example, incorporate the previously mentioned control means 50. The indicators 1102, 1104, 1106, 1108, 1110 may be, for example LEDs, light bulbs, an LCD screen, or other suitable indicators, including, for example, audible indicators.

When the power switch 840 is first turned on, the FULL indicator 1102, the WAIT indicator 1104, the FAULT indicator 1106 and the TEST indicator 1108 will come on for a short time (e.g., 1 second) to provide an indication that these indicators are functioning. Then the indicators 1102, 1106, 1008 will go off.

The WAIT indicator 1104 will remain on long enough for the oxygen sensor 1233 or the concentrator oxygen sensor to reach operating temperature (e.g., 3.0 minutes).

The controller 1100 also monitors the heater current and voltage and the output current voltage of the oxygen sensor 1233 or the concentrator oxygen sensor whenever device 1200 is turned on. If a fault in the oxygen sensor 1233 or the concentrator oxygen sensor is detected at any time, the WAIT indicator 1104 is flashed at a one second rate, the FAULT indicator 1106 is activated and all other indicators are deactivated. In this state, the compressor 1250 and the test mode function will not operate.

If there is an acceptable level of oxygen as sensed by the oxygen sensor 1233 or the concentrator oxygen sensor in the gas applied to the normal mode inlet 1215 (e.g., greater than 90%) the compressor 1250 will run and the FILLING indicator 1110 will be activated. If the high pressure switch 880 is activated, the FULL indicator 1102 will be activated, the FILLING indicator 1110 will be deactivated and compressor 1250 will be deactivated by the controller 1100.

If oxygen sensor 1248 detects an acceptable predetermined level of oxygen, radial compressor 1250 will be allowed to operate. However, should oxygen sensor 1248 detect an amount of oxygen below a predetermined level, the controller will automatically close down or stop the operation of radial compressor 1250. After the oxygen concentration is increased to above the predetermined level, radial compressor 1250 will once again allow it to be operated.

If the high pressure switch 880 is activated during the warm up period (e.g., a full bottle (e.g., 2,000 psi) already attached to the oxygen outlet 825), the FAULT indictor 1106 will be flashed at a one second rate by the controller 1100 and the device 1200 must be reset to operate.

The test mode operation is based upon a value of pressure being present in a test fitting. If the pressure of the gas stream at the test inlet is greater than some predetermined value, then the controller 1100 should temporarily suspend any operation of the radial compressor and then wait a predetermined time (typically 30 sec.) for the gas values to stabilize. Once the timeout period is over, the controller then uses oxygen sensor 1248 to determine whether the feed gas used by the radial compressor for filling the high pressure tank is above a predetermined concentration value.

The operation of the test mode is basically the same whether or not the unit enters or exits the test mode. There is always a delay to make sure the gas stream is within the requirements of the minimum values of oxygen concentration for filling the high pressure tank or testing the gas value in the test mode. This delay is included to make sure the gas stream reaches full value with any change in sources of the gas within the internal plumbing of the system.

Test switch 852 can be either a preset value for a mechanical, pressure operated switch or it can be a pressure sensor on the board that provides an electrical value for the gas pressure present on the test fitting. The main purpose of test switch 852 is to continuously monitor the oxygen concentration of the feed gas for the radial compressor to make sure it is within the requirements of the predetermined oxygen concentration percentage.

While in accordance with the patent statutes the best mode and preferred embodiments have been set forth, the scope of the invention is not limited thereto, but rather by the scope of the attached claims.

What is claimed:

1. An apparatus for supplying oxygen-enriched gas to a patient and to a high pressure storage tank, comprising; a first compressor which receives ambient air; an oxygen concentrator which produces oxygen enriched gas, said oxygen concentrator having an inlet which receives air from said first compressor and an outlet which provides oxygen enriched gas to a product storage tank; a first outlet flow line which operatively delivers said oxygen enriched gas from said product tank to a patient, said flow line having a pressure from about 3 to about 10 psi; a second outlet flow line which operatively delivers said oxygen enriched gas from said product tank to a buffer tank at a pressure from about 12 to about 22 psi, said buffer tank operatively connected by a flow line to a radial compressor, said radial compressor being capable of compressing said oxygen enriched gas and transferring the oxygen enriched gas to a high pressure storage tank, and a prioritizing apparatus which terminates the operation of said radial compressor when the oxygen concentration of said oxygen enriched gas operatively delivered to said radial compressor falls below a predetermined value so that said oxygen enriched gas is continuously supplied to the patient; wherein said high pressure storage tank is capable of storing compressed gas at a pressure between about 21 psi and about 4000 psi.

2. An apparatus according to claim 1, wherein the amount of said oxygen in said patient flow line is at least 80% by volume.

3. An apparatus according to claim 2, wherein said radial compressor includes at least two piston cylinder assemblies radially arranged around a crank shaft, and said piston cylinder assemblies adapted to sequentially compress said oxygen-enriched gas from said first piston assembly through said last piston assembly.

4. An apparatus according to claim 3, wherein said prioritization includes a determination of said oxygen-enriched gas operatively delivered to said radial compressor by an oxygen sensor and the operation of said radial compressor being terminated when said sensed oxygen-enriched gas is below a predetermined oxygen level, and wherein said patient oxygen-enriched gas and said high pressure storage tank has an oxygen concentration of at least 90% by volume.

5. An apparatus according to claim 4, wherein said radial compressor is operated by a power source other than said oxygen-enriched gas from said oxygen concentrator.

6. An apparatus for supplying oxygen-enriched gas to a patient and to a high pressure storage tank, comprising: a low pressure, oxygen-enriched gas patient flow line for use by a patient, wherein said low pressure patient gas flow line is between about 1 psi and 14 psi; a separate moderate pressure, oxygen-enriched gas buffer flow line operatively connected to a buffer tank; said moderate pressure being between about 5 psi and about 21 psi and is greater than said low pressure; said patient flow line and said buffer tank flow line being prioritized so as to continuously supply said oxygen-enriched gas for use by a patient; a radial compressor operated by a power source other than said oxygen enriched gas, said buffer tank solely and operatively connected to said radial compressor; said radial compressor being capable of compressing said oxygen-enriched gas to a high pressure, wherein said high pressure is between about 21 psi and 4000 psi; and a high pressure storage tank for portable storage of said high pressure oxygen-enriched gas.

7. An apparatus according to claim 6, wherein said radial compressor includes at least two piston cylinder assemblies radially arranged around a crank shaft, and said piston cylinder assemblies adapted to sequentially compress said oxygen-enriched gas from said first piston assembly through said last piston assembly.

8. An apparatus according to claim 7, wherein the amount of said oxygen in said patient flow line is at least 80% by volume, and wherein said prioritization includes a determination of the oxygen-enriched gas operatively delivered to said radial compressor by an oxygen sensor and the operation of said radial compressor being terminated when said sensed oxygen-enriched gas is below a predetermined oxygen level.

9. An apparatus according to claim 8, wherein said patient oxygen-enriched gas and said high pressure storage tank has an oxygen concentration of at least 90% by volume, and wherein said patient flow line has an oxygen-enriched gas flow rate of from about 1 to about 6 liters per minute.

10. An apparatus according to claim 9, wherein the pressure in said patient flow line is from about 3 to about 8 psi, wherein the pressure of said oxygen-enriched gas in said buffer flow line is from about 10 to about 22 psi, and wherein said high pressure storage tank is capable of storing said compressed oxygen-enriched gas at a pressure of from about 500 to about 4000 psi.

11. An apparatus according to claim 7, including an oxygen product storage tank and wherein said patient flow line and said buffer tank flow line are independently connected to said oxygen product storage tank.

12. An apparatus according to claim 6, wherein said high pressure storage tank is portable.

13. An apparatus according to claim 8, wherein said high pressure storage tank is portable.

14. An apparatus according to claim 10, wherein said high pressure storage tank is portable.

15. A process for supplying oxygen-enriched gas to a patient and to a high pressure storage tank, comprising the steps of: continuously supplying low pressure oxygen-enriched gas through a patient flow line, wherein said low pressure is between about 1 psi and about 14 psi; separately supplying a moderate pressure, oxygen-enriched gas through a buffer tank flow line to a buffer tank; said moderate pressure being between about 5 psi and about 21 psi and is greater than said low pressure; operatively supplying said oxygen-enriched gas from said buffer tank to a radial compressor; compressing said oxygen enriched gas in said radial compressor and feeding said compressed oxygen-enriched gas to a high pressure storage tank, wherein said high pressure is between about 21 psi and 4000 psi; and prioritizing said patient flow line and said buffer tank flow line so that said patient flow line is continuously supplied with said oxygen-enriched gas.

16. A process according to claim 15, wherein the oxygen concentration in said patient flow line and said buffer tank flow line is at least 75% by volume.

17. A process according to claim 16, wherein the pressure of said oxygen-enriched gas in said storage tank is at least 500 psi, wherein said radial compressor includes at least two piston cylinder assemblies radially arranged around a crank shaft, and said piston cylinder assemblies adapted to sequentially compress said oxygen-enriched gas from said first piston assembly through said last piston assembly.

18. A process according to claim 17, wherein the pressure of said oxygen-enriched gas in said patient flow line is from about 3 to about 10 psi and wherein the pressure of said oxygen-enriched gas in said buffer tank flow line is at a higher pressure.

19. A process according to claim 18, wherein said prioritization includes shutting off said radial compressor when said oxygen-enriched gas thereto is below a predetermined level.

20. A process according to claim 19, wherein the pressure of said oxygen-enriched gas in said high pressure storage tank is at least 1500 psi, and wherein the oxygen concentration in said patient flow line and said buffer tank flow line is at least 90% by volume.

21. A process according to claim 15, wherein said high pressure storage tank is portable.

22. A process according to claim 17, wherein said high pressure storage tank is portable.

23. A process according to claim 18, wherein said high pressure storage tank is portable.

24. A process according to claim 20, wherein said high pressure storage tank is portable.

* * * * *